United States Patent
Chua et al.

(10) Patent No.: US 9,650,644 B2
(45) Date of Patent: May 16, 2017

(54) **GENE SILENCING OF SUGAR-DEPENDENT 1 IN *JATROPHA CURCAS***

(71) Applicant: TEMASEK LIFE SCIENCES LABORATORY LIMITED, Singapore (SG)

(72) Inventors: Nam-Hai Chua, Singapore (SG); Mi Jung Kim, Singapore (SG); Seong Wook Yang, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 14/772,694

(22) PCT Filed: Feb. 25, 2014

(86) PCT No.: PCT/SG2014/000082
§ 371 (c)(1),
(2) Date: Sep. 3, 2015

(87) PCT Pub. No.: WO2014/137289
PCT Pub. Date: Sep. 12, 2014

(65) Prior Publication Data
US 2016/0010097 A1 Jan. 14, 2016

Related U.S. Application Data

(60) Provisional application No. 61/773,386, filed on Mar. 6, 2013.

(51) Int. Cl.
| | | |
|---|---|---|
| C12N 15/82 | (2006.01) | |
| C12N 5/14 | (2006.01) | |
| C07H 21/04 | (2006.01) | |
| C12N 9/20 | (2006.01) | |
| C12N 15/113 | (2010.01) | |

(52) U.S. Cl.
CPC .......... *C12N 15/8247* (2013.01); *C12N 9/20* (2013.01); *C12N 15/1137* (2013.01); *C12N 15/8218* (2013.01); *C07H 21/04* (2013.01); *C12N 5/14* (2013.01); *C12N 2310/14* (2013.01); *C12Y 301/01003* (2013.01)

(58) Field of Classification Search
None
See application file for complete search history.

(56) References Cited

PUBLICATIONS

Kelly, A.A., "Seed Storage Oil Mobilization is Important But Not Essential for Germination or Seedling Establishment in Arabidopsis," Plant Physiology, 2011, vol. 157, pp. 866-875, copyright 2011 American Society of Plant Biologists.
Eastmond, P.J., "Sugar-Dependent1 Encodes a Patatin Domain Triacylglycerol Lipase That Initiates Storage Oil Breakdown in Germinating Arabidopsis Seeds," The Plant Cell, vol. 18, pp. 665-675, copyright 2006 American Society of Plant Biologists.
Kelly, A.A., "Suppression of the Sugar-Dependent1 Triacylglycerol Lipase Family During Seed Development Enhances Oil Yield in Oilseed Rape (Brassica napus L.)," Plant Bioechnology Journal, 2013, vol. 11, pp. 355-361, Published online: Nov. 21, 2012.
Kim, M.J., "Gene Silencing of Sugar-Dependent 1 (JcSDP1), Encoding a Patatin-Domain Triacylglycerol Lipase, Enhances Seed Oil Accumulation in Jatropha Curcas," Biotechnology for Biofuels, 2014, vol. 7, No. 36, pp. 1-16.
International Search Report mailed Apr. 2, 2014, Form PCT/ISA/210, International Application No. PCT/SG2014/000082, Filing date: Feb. 25, 2014, Applicant: Temasek Life Sciences Laboratory Limited, 4 pages.
Invitation to Respond to Written Opinion issued in Singapore Application No. 11201506973V, dated Jul. 1, 2016, 7 pages.

*Primary Examiner* — Matthew Keogh
(74) *Attorney, Agent, or Firm* — Rothwell, Figg, Ernst & Manbeck, P.C.

(57) ABSTRACT

The present invention relates to the field of plant molecular biology and gene silencing. More particularly, the present invention relates to gene silencing of Sugar-dependent 1 (JcSDP1) in *Jatropha curcas*. JcSDP1 encodes a patatin-domain triacylglyerol lipase. Silencing of JcSDP1 enhances seed oil accumulation in *J. curcas*.

22 Claims, 13 Drawing Sheets

```
JcSDP1    MDISNEANVDPFPIGPSSIIGRTIAFRVLFCKSMGQLRRRIYHFLLNYICRLRDFCASMV    60
AtSDP1    MDISNEASVDPFSIGPSSIMGRTIAFRVLFCRSMSQLRRDLFRFLLHWFLRFKLTVSPFV    60
          *******.****.*****:*****************:**:****.:*:**::: *::  ::.*

RXXL
JcSDP1    SWLHPRNPQGILAMVTIIAFVLKRYTNVKSRAEMAYRRKFWRNMMRTALTYEEWAHAAKM   120
AtSDP1    SWFHPRNPQGILAVVTIIAFVLKRYTNVKIKAEMAYRRKFWRNMMRTALTYEEWAHAAKM   120
          **:**********:***************  :************************.************
                           RXXL                  RXXL
JcSDP1    LDKETPKMNESDLYDEELVRNKLQELRHRRQEGSLRDIIFCMRADLIRNLGNMCNPELHK   180
AtSDP1    LEKETPKMNESDLYDEELVKNKLQELRHRRQEGSLRDIMFCMRADLVRNLGNMCNSELHK   180
          *:*****************:******************:*******:********.:****
                                          RXXL     GXGXX
JcSDP1    GRLQVPKLIKEYIDEVSTQLRMVCDSDTEELSLEEKLSFMHETRHAFGRTALLLSGGASL   240
AtSDP1    GRLQVPRHIKEYIDEVSTQLRMVCNSDSEELSLEEKLSFMHETRHAFGRTALLLSGGASL   240
          ******::****************:**:*****************************.************
                   GXSXG
JcSDP1    GAFHVGVVKTLVQHKLLPRIIAGSSVGSIMCSIVATRAWPELQSFFEDSLHSLQFFDQMG   300
AtSDP1    GAFHVGVVRTLVEHKLLPRIIAGSSVGSIICAVVASRSWPELQSFFENSLHSLQFFDQLG   300
          *******:***::***************:*::**:*:*********:.********:.*
          G
JcSDP1    GLFTVVKRVTTQGAVHEIRQLQWMLRHLTSNLTFQEAYDMTGRILAITVCSPRKHEPPRC   360
AtSDP1    GVFSIVKRVMTQGALHDIRQLQCMLRNLTSNLTFQEAYDMTGRILGITVCSPRKHEPPRC   360
          *:*::****  *****.*  ****:.*******************.*************
```

FIGURE 3

A) Con't

```
JcSDP1  LNYLTSPHVVIWSAVTASCAFPGLFEAQELMAKDRSGEIVPYHPPFKLEPEEGS-STSAR  419
AtSDP1  LNYLTSPHVVIWSAVTASCAFPGLFEAQELMAKDRSGEIVPYHPPFNLDPEVGTKSSSGR  420
        ***********************************************:;** *; *;*.

JcSDP1  RWRDGSLEIDLPMMQLKELFNVNHFIVSQANPHIAPLLRMKEFIRAYGGNFAAKLAHLTE  479
AtSDP1  RWRDGSLEVDLPMMQLKELFNVNHFIVSQANPHIAPLLRLKDLVRAYGGRFAAKLAHLVE  480
        ********.************************** **:;::********. *******.*

JcSDP1  MEVKHRCSQVLELGFPLGGVAKLFAQDWEGDVTVVMPATLAQYSKIIQNPTLVELQKAAN  539
AtSDP1  MEVKHRCNQVLELGFPLGGLAKLFAQEWEGDVTVVMPATLAQYSKIIQNPTHVELQKAAN  540
        *******.***********.******:***********************:********

JcSDP1  QGRRCTWEKLSAIKANCGIELCLDECVAILNHMRRLKRSAERAAAASHGIPNPSTSNVKF  599
AtSDP1  QGRRCTWEKLSAIKSNCGIELALDDSVAILNHMRRLKKSAERAATATSSSHHGLASTTRF  600
        **************;*****.**:.************:******:***;: : *;..;*

JcSDP1  SASRRIPSWNCIARENSTGSIDELLTDVASTFHQGVGGSGATTGRNLRTHRNIHDGSDSE  659
AtSDP1  NASRRIPSWNVLARENSTGSLDDDLVTDNN------LHASSGRNL------SDSE  642
        .*********  ;*********:**::;**:**               *:;*****    ****

JcSDP1  SENVDITSWTRSGGPLMRTTSANKFIDFVQNLDIDAELTKGLLTHPNSPGAPMGIRDPFN  719
AtSDP1  TESVELSSWTRTGGPLMRTASANKFIDFVQSLDIDIALVRGFSSSPNSPAVPPGG--SFT  700
        :*.*:::**** ;****** ;********:****  ; **:**..** ;         **.*.

JcSDP1  TSSRVTTPERISESDFELRDFSRSSQTGSSIMVTEGDLLQPERIHNGIVLNVVKKENLGL  779
AtSDP1  PSPRSIAAHSDIESNSNSNNLGTST---SSITVTEGDLLQPERTSNGFVLNVVKRENLGM  757
        .*.*  :  ;  ***; ;  :  *;      *** ***********  ;*** ******;****;
```

FIGURE 3

A) Con't

```
JcSDP1    SNRSQDSENYNEIPECVQLDR---DMDGSSASEYAGDDDDDNDNDNDIITVTNFSNVVS  836
AtSDP1    PSIGNQN---TELPESVQLDIPEKEMDCSSVSEHEEDDNDNEEHNG-----------SS  803
          . .::.  .:***.****   .:** **.**: **:.:::::::             *

JcSDP1    PIPVPKDDSGVHEGQDQSSVDG  858
AtSDP1    LVTVSSEDSGLQEPVSGSVIDA  825
          :.*...:****::*  . .*.
```

B)

Figure 5
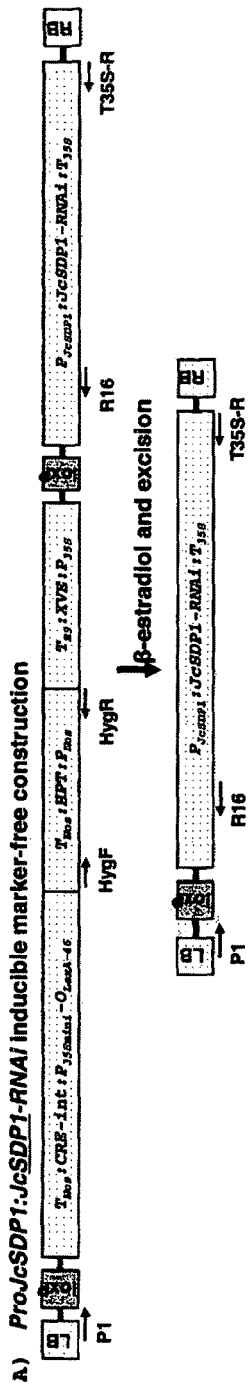
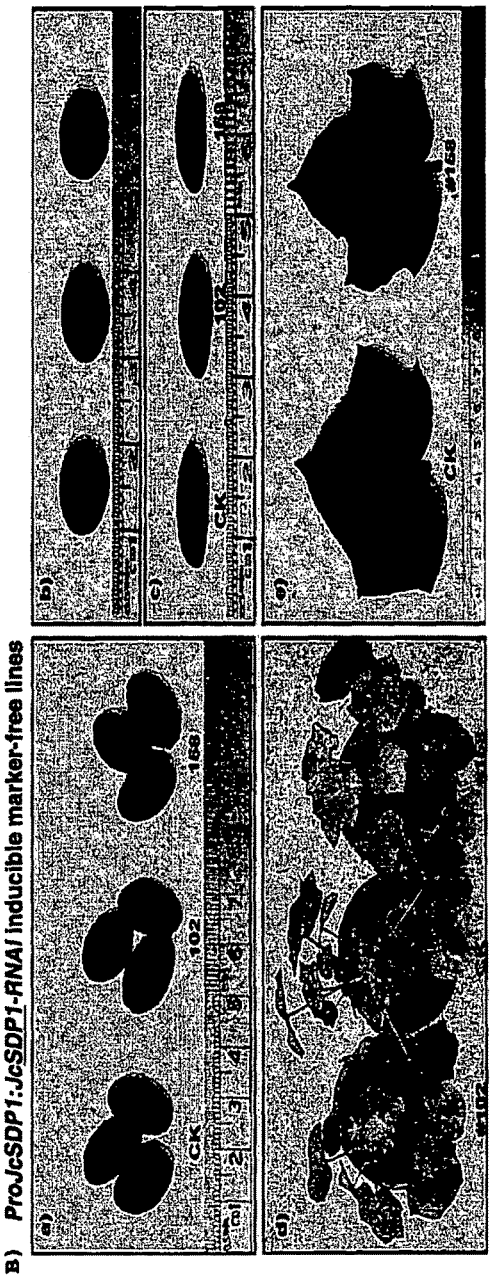

Figure 5 Con't.
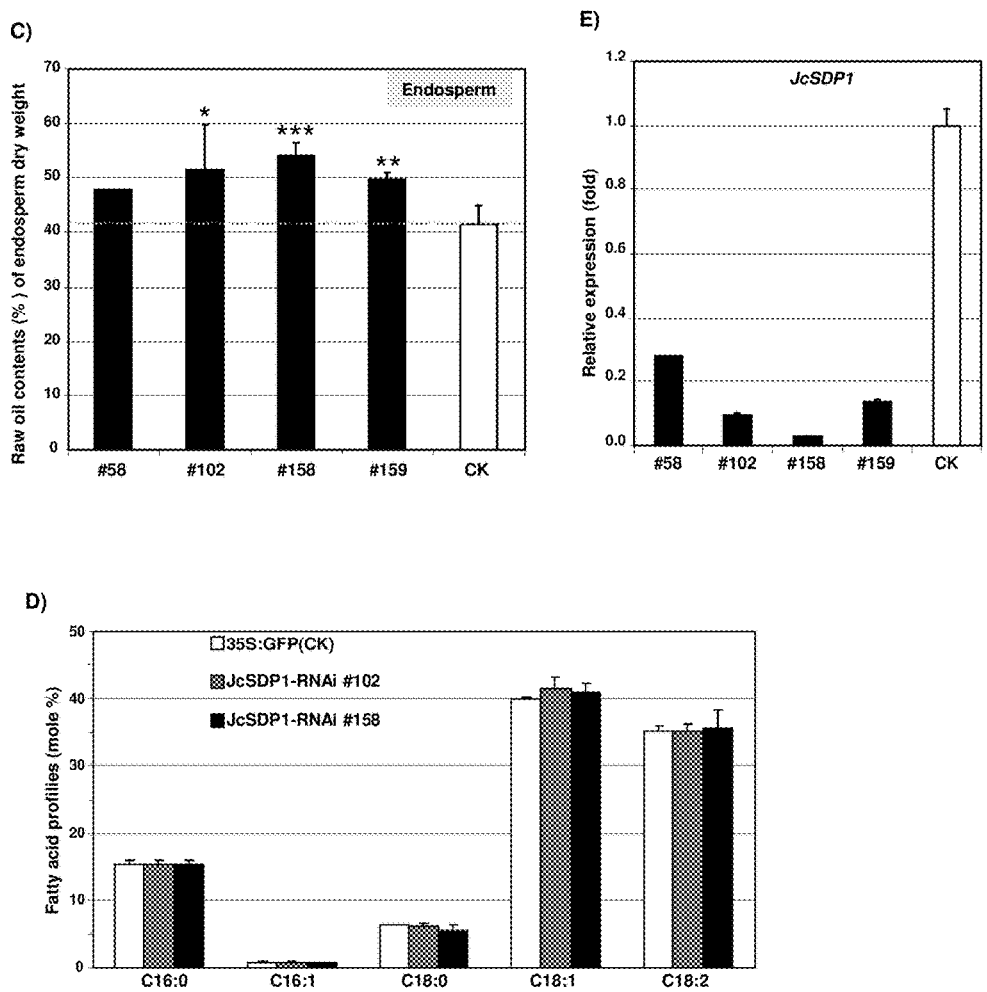

SEQUENCE LISTING

<160> NUMBER OF SEQ ID NOS: 58

<210> SEQ ID NO 1
<211> LENGTH: 3835
<212> TYPE: DNA
<213> ORGANISM: Jatropha curcas
<220> FEATURE:
<221> NAME/KEY: promoter
<222> LOCATION: (1)..(722)

```
<220> FEATURE:
<221> NAME/KEY: 5'UTR
<222> LOCATION: (723)..(873)
<220> FEATURE:
<221> NAME/KEY: CDS
<222> LOCATION: (874)..(3450)
<220> FEATURE:
<221> NAME/KEY: 3'UTR
<222> LOCATION: (3451)..(3835)

<400> SEQUENCE: 1
tacatccagt agattgcacg tcacacacta atctacccgc cacgtatgtg cccattcaaa    60
ctttgcgtca ctgtatcgct atctttatct ctttcacgtt tcccaatatt ttccctctct   120
tctctcctta tagtaaagcc tatcaaccag tccccatctg tctctctcac tctataaagc   180
cacgtttttt cttcttttcc cgggattatc ctatctgggt ttctcgggtt tcttttgaa    240 ttccaattcc tgagttcgtt gccctttttc tgttttctg tttgtttacg ttatgaatac    300
ccatttggta tttgtattaa ttaaatagct ggtatatgtt atttgtgctt tttaggtttg   360
agggttttgg ggtttggtta atcagcaaga tctgttaaga aagaaaggaa ggtgagagtt   420
gagaggacag acccatttgg ctgcttttct tggaatttca atatttaagg ttggctttct   480
gctgaattcg gttaagaggc tggattttgt gacttctata catccctttg gtgtataaat   540
taagttttct tataggattg ctatctatcc acttttatct aacaaaagcc attatctttc   600
ttttgcatag agagtctggt ggtgtaatat ttcaatcatt ttgtgattgg agaaacaatt   660
tcagtcattt tattgtcttt atgcaattgt tagagctgtg cagaacatat aggtgtatat   720
agtcaaaaca ttgccttgta attccttcaa ttgctgtctc ctagcaattg ttattgcttc   780
ttaagtttta tattagcaaa tattcttgtt gagttacagg aattcccaat agcttcgatt   840
tagcaaatca tccaaaacac gaaacttttta gag atg gat ata agt aat gag gcc    894
                                     Met Asp Ile Ser Asn Glu Ala
                                      1               5 aat gtt gat ccc ttt cca att gga cct tca tca att att ggt aga act    942
Asn Val Asp Pro Phe Pro Ile Gly Pro Ser Ser Ile Ile Gly Arg Thr
         10                  15                  20 att gct ttt aga gtg tta ttc tgc aag tca atg gga caa ttg agg cgt    990
Ile Ala Phe Arg Val Leu Phe Cys Lys Ser Met Gly Gln Leu Arg Arg
 25                  30                  35 aga atc tat cat ttt tta ttg aat tac att tgt aga ctt agg gat ttt   1038
Arg Ile Tyr His Phe Leu Leu Asn Tyr Ile Cys Arg Leu Arg Asp Phe
 40                  45                  50                  55 tgt gct tca atg gta tca tgg ttg cat ccg cgg aat cca caa gga ata   1086
Cys Ala Ser Met Val Ser Trp Leu His Pro Arg Asn Pro Gln Gly Ile
             60                  65                  70 ctg gca atg gtg aca ata att gct ttt gta ttg aaa agg tac aca aac   1134
Leu Ala Met Val Thr Ile Ile Ala Phe Val Leu Lys Arg Tyr Thr Asn
         75                  80                  85 gtg aaa tcg agg gct gag atg gca tat cgg agg aaa ttt tgg agg aat   1182
Val Lys Ser Arg Ala Glu Met Ala Tyr Arg Arg Lys Phe Trp Arg Asn
 90                  95                 100 atg atg aga act gca ttg aca tat gaa gag tgg gca cat gct gct aag   1230
Met Met Arg Thr Ala Leu Thr Tyr Glu Glu Trp Ala His Ala Ala Lys
        105                 110                 115 atg ctt gat aaa gag aca cca aag atg aac gaa tcg gac ctt tat gat   1278
Met Leu Asp Lys Glu Thr Pro Lys Met Asn Glu Ser Asp Leu Tyr Asp
120                 125                 130                 135 gaa gaa tta gtg aga aat aag ctt cag gag ctt cga cac cgt aga caa   1326
Glu Glu Leu Val Arg Asn Lys Leu Gln Glu Leu Arg His Arg Arg Gln
                140                 145                 150
```

| | |
|---|---|
| gag gga tct ctt aga gat att atc ttt tgt atg aga gct gat ctt ata<br>Glu Gly Ser Leu Arg Asp Ile Ile Phe Cys Met Arg Ala Asp Leu Ile<br>155 160 165 | 1374 |
| aga aat ctt ggt aat atg tgc aac cca gag ctt cac aag ggc agg ctt<br>Arg Asn Leu Gly Asn Met Cys Asn Pro Glu Leu His Lys Gly Arg Leu<br>170 175 180 | 1422 |
| caa gtg cct aag ctt att aag gaa tac att gat gag gtc tca acc cag<br>Gln Val Pro Lys Leu Ile Lys Glu Tyr Ile Asp Glu Val Ser Thr Gln<br>185 190 195 | 1470 |
| ttg aga atg gtt tgt gac tca gat aca gag gag ctt tca ttg gag gaa<br>Leu Arg Met Val Cys Asp Ser Asp Thr Glu Glu Leu Ser Leu Glu Glu<br>200 205 210 215 | 1518 |
| aag ctt tct ttc atg cat gaa acg aga cat gca ttt ggg aga aca gct<br>Lys Leu Ser Phe Met His Glu Thr Arg His Ala Phe Gly Arg Thr Ala<br>220 225 230 | 1566 |
| ttg ctt ttg agt gga ggt gct tcc ctc gga gcc ttt cat gta ggt gtg<br>Leu Leu Leu Ser Gly Gly Ala Ser Leu Gly Ala Phe His Val Gly Val<br>235 240 245 | 1614 |
| gtt aag acg ctg gtg cag cat aag ctt ttg ccc aga ata att gct ggt<br>Val Lys Thr Leu Val Gln His Lys Leu Leu Pro Arg Ile Ile Ala Gly<br>250 255 260 | 1662 |
| tct agt gta gga tcc att atg tgt tct att gtc gcc acg aga gca tgg<br>Ser Ser Val Gly Ser Ile Met Cys Ser Ile Val Ala Thr Arg Ala Trp<br>265 270 275 | 1710 |
| cca gag ttg caa agt ttt ttt gaa gat tct ttg cat tca ttg cag ttt<br>Pro Glu Leu Gln Ser Phe Phe Glu Asp Ser Leu His Ser Leu Gln Phe<br>280 285 290 295 | 1758 |
| ttt gat caa atg ggc ggg ctt ttt act gta gtc aag agg gtc acg aca<br>Phe Asp Gln Met Gly Gly Leu Phe Thr Val Val Lys Arg Val Thr Thr<br>300 305 310 | 1806 |
| caa ggt gct gtc cat gaa ata cgg cag ttg caa tgg atg tta agg cat<br>Gln Gly Ala Val His Glu Ile Arg Gln Leu Gln Trp Met Leu Arg His<br>315 320 325 | 1854 |
| ctc aca agc aat ctt aca ttt cag gaa gct tat gat atg aca ggt cga<br>Leu Thr Ser Asn Leu Thr Phe Gln Glu Ala Tyr Asp Met Thr Gly Arg<br>330 335 340 | 1902 |
| att ctt gca atc aca gtt tgc tct cca agg aag cat gag cct cct aga<br>Ile Leu Ala Ile Thr Val Cys Ser Pro Arg Lys His Glu Pro Pro Arg<br>345 350 355 | 1950 |
| tgc ctt aac tac ctg act tca cct cat gtt gtc ata tgg agt gca gtc<br>Cys Leu Asn Tyr Leu Thr Ser Pro His Val Val Ile Trp Ser Ala Val<br>360 365 370 375 | 1998 |
| act gct tct tgt gcc ttt cct ggt ctt ttt gaa gcc cag gaa ctt atg<br>Thr Ala Ser Cys Ala Phe Pro Gly Leu Phe Glu Ala Gln Glu Leu Met<br>380 385 390 | 2046 |
| gct aag gat aga agt gga gaa att gtt cca tat cat cca ccc ttc aag<br>Ala Lys Asp Arg Ser Gly Glu Ile Val Pro Tyr His Pro Pro Phe Lys<br>395 400 405 | 2094 |
| ctg gaa cca gag gaa ggg tca agc acg tct gct cgt cgg tgg agg gat<br>Leu Glu Pro Glu Glu Gly Ser Ser Thr Ser Ala Arg Arg Trp Arg Asp<br>410 415 420 | 2142 |
| gga agc ttg gag att gat tta cct atg atg caa ttg aag gag cta ttc<br>Gly Ser Leu Glu Ile Asp Leu Pro Met Met Gln Leu Lys Glu Leu Phe<br>425 430 435 | 2190 |
| aat gtt aat cat ttt att gtg agt caa gca aat cct cac att gct cca<br>Asn Val Asn His Phe Ile Val Ser Gln Ala Asn Pro His Ile Ala Pro<br>440 445 450 455 | 2238 |
| tta ttg aga atg aag gag ttt ata aga gct tat ggc ggt aac ttt gct<br>Leu Leu Arg Met Lys Glu Phe Ile Arg Ala Tyr Gly Gly Asn Phe Ala | 2286 |

```
                460                 465                 470
gca aag ctt gct cat ctc acc gag atg gaa gta aaa cat aga tgc agt    2334
Ala Lys Leu Ala His Leu Thr Glu Met Glu Val Lys His Arg Cys Ser
        475                 480                 485 cag gtg ttg gaa ctt ggt ttt cca tta ggt gga gtt gcc aag ctt ttt    2382
Gln Val Leu Glu Leu Gly Phe Pro Leu Gly Gly Val Ala Lys Leu Phe
            490                 495                 500 gct caa gat tgg gag gga gac gtc act gtt gtt atg cct gct aca ctc    2430
Ala Gln Asp Trp Glu Gly Asp Val Thr Val Val Met Pro Ala Thr Leu
505                 510                 515 gct cag tac tca aaa att ata caa aat ccg act ctt gtg gag ctg caa    2478
Ala Gln Tyr Ser Lys Ile Ile Gln Asn Pro Thr Leu Val Glu Leu Gln
520                 525                 530                 535 aag gcg gcc aac caa ggg aga agg tgt aca tgg gag aaa ctt tca gcc    2526
Lys Ala Ala Asn Gln Gly Arg Arg Cys Thr Trp Glu Lys Leu Ser Ala
                540                 545                 550 ata aaa gcc aac tgc ggg att gag ctt tgt ctt gat gaa tgt gtc gca    2574
Ile Lys Ala Asn Cys Gly Ile Glu Leu Cys Leu Asp Glu Cys Val Ala
            555                 560                 565 att ctc aac cac atg cgt aga ctc aaa agg agt gct gag aga gca gct    2622
Ile Leu Asn His Met Arg Arg Leu Lys Arg Ser Ala Glu Arg Ala Ala
        570                 575                 580 gct gct tcg cat ggc ata cct aac cca agt act agt aat gtc aaa ttc    2670
Ala Ala Ser His Gly Ile Pro Asn Pro Ser Thr Ser Asn Val Lys Phe
585                 590                 595 agt gct tct aga aga atc cct tct tgg aac tgc att gct aga gag aac    2718
Ser Ala Ser Arg Arg Ile Pro Ser Trp Asn Cys Ile Ala Arg Glu Asn
600                 605                 610                 615 tca aca ggg tca att gat gag ctt ctg act gat gtt gct tcc aca ttt    2766
Ser Thr Gly Ser Ile Asp Glu Leu Leu Thr Asp Val Ala Ser Thr Phe
                620                 625                 630 cat caa ggt gtt ggt gga tct gga gca act aca ggt aga aat ttg cgg    2814
His Gln Gly Val Gly Gly Ser Gly Ala Thr Thr Gly Arg Asn Leu Arg
            635                 640                 645 act cac cgc aac ata cat gat gga agc gac agc gaa tct gaa aat gta    2862
Thr His Arg Asn Ile His Asp Gly Ser Asp Ser Glu Ser Glu Asn Val
        650                 655                 660 gat ata act tct tgg aca agg tct ggt ggg cca ttg atg agg aca act    2910
Asp Ile Thr Ser Trp Thr Arg Ser Gly Gly Pro Leu Met Arg Thr Thr
665                 670                 675 tca gca aat aaa ttt att gac ttc gtt caa aat ctt gat att gat gcc    2958
Ser Ala Asn Lys Phe Ile Asp Phe Val Gln Asn Leu Asp Ile Asp Ala
680                 685                 690                 695 gaa ttg acc aaa ggc ttg ttg act cat cct aac tct ccg ggg gct cct    3006
Glu Leu Thr Lys Gly Leu Leu Thr His Pro Asn Ser Pro Gly Ala Pro
                700                 705                 710 atg gga att agg gat cca ttt aat aca agt tct cgg gtg aca aca cct    3054
Met Gly Ile Arg Asp Pro Phe Asn Thr Ser Ser Arg Val Thr Thr Pro
            715                 720                 725 gag aga att tcg gaa agt gat ttt gaa ctg agg gat ttt agc aga tca    3102
Glu Arg Ile Ser Glu Ser Asp Phe Glu Leu Arg Asp Phe Ser Arg Ser
        730                 735                 740 tct cag act ggt tct agt att atg gtt act gaa ggc gat ctt ttg cag    3150
Ser Gln Thr Gly Ser Ser Ile Met Val Thr Glu Gly Asp Leu Leu Gln
745                 750                 755 cca gaa aga atc cat aat ggg att gtg ttg aac gtc gta aag aag gaa    3198
Pro Glu Arg Ile His Asn Gly Ile Val Leu Asn Val Val Lys Lys Glu
760                 765                 770                 775 aac ttg gga ctc tca aat aga agc cag gat tca gaa aat tac aat gaa    3246
```

```
Asn Leu Gly Leu Ser Asn Arg Ser Gln Asp Ser Glu Asn Tyr Asn Glu
                780                 785                 790 att cct gaa tgt gtt cag ctt gat agg gat atg gat ggt agc tca gca    3294
Ile Pro Glu Cys Val Gln Leu Asp Arg Asp Met Asp Gly Ser Ser Ala
        795                 800                 805 tct gaa tat gct ggg gat gac gat gat gac gac aat gac aat gac aat    3342
Ser Glu Tyr Ala Gly Asp Asp Asp Asp Asp Asp Asn Asp Asn Asp Asn
    810                 815                 820 gac atc att act gta aca aac ttc tca aat gtg gta tct ccc att cct    3390
Asp Ile Ile Thr Val Thr Asn Phe Ser Asn Val Val Ser Pro Ile Pro
825                 830                 835 gtt ccc aag gat gat tct ggg gta cat gag gga cag gat caa agt tct    3438
Val Pro Lys Asp Asp Ser Gly Val His Glu Gly Gln Asp Gln Ser Ser
840                 845                 850                 855 gtg gat ggt tag ttttgaggaa tatttctgtt gtgtgaacaa tttggtctat        3490
Val Asp Gly ctgattcccg gatcacctta atatcaagtg ccactagctg cagaaagagc agagaaaagc  3550
aattattgct tgaacatccc catttcacgt cgttttcagg ataatggt cagggacagc    3610 agagaataat caatcatttg ttagatagaa gatttgtata tgaaaccgga gagaaaagct  3670 caacatttt agaagaatga tcgcatttga gatcaaattg tcttgaatat gccaaattat   3730
ttattgtgta aatgtattg tacataccac gcaatgtgca atgtgatttt catacgtaca   3790
gttcaatgaa agaaacagat tttacatcaa aaaaaaaaa aaaaa                   3835

<210> SEQ ID NO 2
<211> LENGTH: 858
<212> TYPE: PRT
<213> ORGANISM: Jatropha curcas

<400> SEQUENCE: 2

Met Asp Ile Ser Asn Glu Ala Asn Val Asp Pro Phe Pro Ile Gly Pro
1               5                   10                  15

Ser Ser Ile Ile Gly Arg Thr Ile Ala Phe Arg Val Leu Phe Cys Lys
                20                  25                  30

Ser Met Gly Gln Leu Arg Arg Arg Ile Tyr His Phe Leu Leu Asn Tyr
            35                  40                  45

Ile Cys Arg Leu Arg Asp Phe Cys Ala Ser Met Val Ser Trp Leu His
        50                  55                  60

Pro Arg Asn Pro Gln Gly Ile Leu Ala Met Val Thr Ile Ile Ala Phe
65                  70                  75                  80

Val Leu Lys Arg Tyr Thr Asn Val Lys Ser Arg Ala Glu Met Ala Tyr
                85                  90                  95

Arg Arg Lys Phe Trp Arg Asn Met Met Arg Thr Ala Leu Thr Tyr Glu
                100                 105                 110

Glu Trp Ala His Ala Ala Lys Met Leu Asp Lys Glu Thr Pro Lys Met
            115                 120                 125

Asn Glu Ser Asp Leu Tyr Asp Glu Leu Val Arg Asn Lys Leu Gln
        130                 135                 140

Glu Leu Arg His Arg Arg Gln Glu Gly Ser Leu Arg Asp Ile Ile Phe
145                 150                 155                 160

Cys Met Arg Ala Asp Leu Ile Arg Asn Leu Gly Asn Met Cys Asn Pro
                165                 170                 175

Glu Leu His Lys Gly Arg Leu Gln Val Pro Lys Leu Ile Lys Glu Tyr
            180                 185                 190

Ile Asp Glu Val Ser Thr Gln Leu Arg Met Val Cys Asp Ser Asp Thr
```

```
            195                 200                 205
Glu Glu Leu Ser Leu Glu Glu Lys Leu Ser Phe Met His Glu Thr Arg
    210                 215                 220

His Ala Phe Gly Arg Thr Ala Leu Leu Leu Ser Gly Gly Ala Ser Leu
225                 230                 235                 240

Gly Ala Phe His Val Gly Val Val Lys Thr Leu Val Gln His Lys Leu
                245                 250                 255

Leu Pro Arg Ile Ile Ala Gly Ser Ser Val Gly Ser Ile Met Cys Ser
            260                 265                 270

Ile Val Ala Thr Arg Ala Trp Pro Glu Leu Gln Ser Phe Phe Glu Asp
        275                 280                 285

Ser Leu His Ser Leu Gln Phe Phe Asp Gln Met Gly Gly Leu Phe Thr
    290                 295                 300

Val Val Lys Arg Val Thr Thr Gln Gly Ala Val His Glu Ile Arg Gln
305                 310                 315                 320

Leu Gln Trp Met Leu Arg His Leu Thr Ser Asn Leu Thr Phe Gln Glu
                325                 330                 335

Ala Tyr Asp Met Thr Gly Arg Ile Leu Ala Ile Thr Val Cys Ser Pro
            340                 345                 350

Arg Lys His Glu Pro Pro Arg Cys Leu Asn Tyr Leu Thr Ser Pro His
        355                 360                 365

Val Val Ile Trp Ser Ala Val Thr Ala Ser Cys Ala Phe Pro Gly Leu
    370                 375                 380

Phe Glu Ala Gln Glu Leu Met Ala Lys Asp Arg Ser Gly Glu Ile Val
385                 390                 395                 400

Pro Tyr His Pro Pro Phe Lys Leu Glu Pro Glu Gly Ser Ser Thr
                405                 410                 415

Ser Ala Arg Arg Trp Arg Asp Gly Ser Leu Glu Ile Asp Leu Pro Met
            420                 425                 430

Met Gln Leu Lys Glu Leu Phe Asn Val Asn His Phe Ile Val Ser Gln
        435                 440                 445

Ala Asn Pro His Ile Ala Pro Leu Leu Arg Met Lys Glu Phe Ile Arg
    450                 455                 460

Ala Tyr Gly Gly Asn Phe Ala Ala Lys Leu Ala His Leu Thr Glu Met
465                 470                 475                 480

Glu Val Lys His Arg Cys Ser Gln Val Leu Glu Leu Gly Phe Pro Leu
                485                 490                 495

Gly Gly Val Ala Lys Leu Phe Ala Gln Asp Trp Glu Gly Asp Val Thr
            500                 505                 510

Val Val Met Pro Ala Thr Leu Ala Gln Tyr Ser Lys Ile Ile Gln Asn
        515                 520                 525

Pro Thr Leu Val Glu Leu Gln Lys Ala Ala Asn Gly Arg Arg Cys
    530                 535                 540

Thr Trp Glu Lys Leu Ser Ala Ile Lys Ala Asn Cys Gly Ile Glu Leu
545                 550                 555                 560

Cys Leu Asp Glu Cys Val Ala Ile Leu Asn His Met Arg Arg Leu Lys
                565                 570                 575

Arg Ser Ala Glu Arg Ala Ala Ala Ser His Gly Ile Pro Asn Pro
            580                 585                 590

Ser Thr Ser Asn Val Lys Phe Ser Ala Ser Arg Ile Pro Ser Trp
        595                 600                 605

Asn Cys Ile Ala Arg Glu Asn Ser Thr Gly Ser Ile Asp Glu Leu Leu
    610                 615                 620
```

Thr Asp Val Ala Ser Thr Phe His Gln Gly Val Gly Ser Gly Ala
625                 630                 635                 640

Thr Thr Gly Arg Asn Leu Arg Thr His Arg Asn Ile His Asp Gly Ser
            645                 650                 655

Asp Ser Glu Ser Glu Asn Val Asp Ile Thr Ser Trp Thr Arg Ser Gly
        660                 665                 670

Gly Pro Leu Met Arg Thr Thr Ser Ala Asn Lys Phe Ile Asp Phe Val
        675                 680                 685

Gln Asn Leu Asp Ile Asp Ala Glu Leu Thr Lys Gly Leu Leu Thr His
    690                 695                 700

Pro Asn Ser Pro Gly Ala Pro Met Gly Ile Arg Asp Pro Phe Asn Thr
705                 710                 715                 720

Ser Ser Arg Val Thr Thr Pro Glu Arg Ile Ser Glu Ser Asp Phe Glu
                725                 730                 735

Leu Arg Asp Phe Ser Arg Ser Ser Gln Thr Gly Ser Ser Ile Met Val
            740                 745                 750

Thr Glu Gly Asp Leu Leu Gln Pro Glu Arg Ile His Asn Gly Ile Val
        755                 760                 765

Leu Asn Val Val Lys Lys Glu Asn Leu Gly Leu Ser Asn Arg Ser Gln
    770                 775                 780

Asp Ser Glu Asn Tyr Asn Glu Ile Pro Glu Cys Val Gln Leu Asp Arg
785                 790                 795                 800

Asp Met Asp Gly Ser Ser Ala Ser Glu Tyr Ala Gly Asp Asp Asp Asp
                805                 810                 815

Asp Asp Asn Asp Asn Asp Ile Ile Thr Val Thr Asn Phe Ser
            820                 825                 830

Asn Val Val Ser Pro Ile Pro Val Pro Lys Asp Ser Gly Val His
    835                 840                 845

Glu Gly Gln Asp Gln Ser Ser Val Asp Gly
    850                 855

```
<210> SEQ ID NO 3
<211> LENGTH: 2053
<212> TYPE: DNA
<213> ORGANISM: Artificial Sequence
<220> FEATURE:
<223> OTHER INFORMATION: RNAi sequence
<220> FEATURE:
<221> NAME/KEY: misc_feature
<222> LOCATION: (1)..(6)
<223> OTHER INFORMATION: ApaI site
<220> FEATURE:
<221> NAME/KEY: misc_feature
<222> LOCATION: (7)..(879)
<223> OTHER INFORMATION: JcSPD1 promoter and 5' UTR
<220> FEATURE:
<221> NAME/KEY: misc_feature
<222> LOCATION: (880)..(885)
<223> OTHER INFORMATION: XhoI site
<220> FEATURE:
<221> NAME/KEY: misc_feature
<222> LOCATION: (886)..(1253)
<223> OTHER INFORMATION: RNAi sense
<220> FEATURE:
<221> NAME/KEY: misc_feature
<222> LOCATION: (1254)..(1259)
<223> OTHER INFORMATION: HindIII site
<220> FEATURE:
<221> NAME/KEY: misc_feature
<222> LOCATION: (1260)..(1262)
<223> OTHER INFORMATION: linker sequence
<220> FEATURE:
<221> NAME/KEY: misc_feature
```

```
<222> LOCATION: (1263)..(1418)
<223> OTHER INFORMATION: Intron sequence
<220> FEATURE:
<221> NAME/KEY: misc_feature
<222> LOCATION: (1419)..(1424)
<223> OTHER INFORMATION: linker sequence
<220> FEATURE:
<221> NAME/KEY: misc_feature
<222> LOCATION: (1425)..(1430)
<223> OTHER INFORMATION: PstI site
<220> FEATURE:
<221> NAME/KEY: misc_feature
<222> LOCATION: (1431)..(1797)
<223> OTHER INFORMATION: RNAi antisense
<220> FEATURE:
<221> NAME/KEY: misc_feature
<222> LOCATION: (1798)..(1803)
<223> OTHER INFORMATION: BamHI site
<220> FEATURE:
<221> NAME/KEY: misc_feature
<222> LOCATION: (1804)..(1809)
<223> OTHER INFORMATION: linker sequence
<220> FEATURE:
<221> NAME/KEY: misc_feature
<222> LOCATION: (1810)..(1815)
<223> OTHER INFORMATION: XbaI site
<220> FEATURE:
<221> NAME/KEY: misc_feature
<222> LOCATION: (1816)..(2041)
<223> OTHER INFORMATION: T35S
<220> FEATURE:
<221> NAME/KEY: misc_feature
<222> LOCATION: (2042)..(2053)
<223> OTHER INFORMATION: PmlI site

<400> SEQUENCE: 3
gggccctaca tccagtagat tgcacgtcac acactaatct acccgccacg tatgtgccca      60
ttcaaacttt gcgtcactgt atcgctatct ttatctcttt cacgtttccc aatatttttcc    120 ctctcttctc tccttatagt aaagcctatc aaccagtccc catctgtctc tctcactcta    180
taaagccacg ttttttcttc ttttcccggg attatcctat ctgggtttct cgggtttctt    240
tttgaattcc aattcctgag ttcgttgccc ttttttctgtt tttctgtttg tttacgttat    300
gaatacccat ttggtatttg tattaattaa atagctggta tatgttattt gtgcttttta    360
ggtttgaggg ttttggggtt tggttaatca gcaagatctg ttaagaaaga aaggaaggtg    420
agagttgaga ggacagaccc atttggctgc ttttcttgga atttcaatat ttaaggttgg    480 cttttctgctg aattcggtta agaggctgga ttttgtgact tctatacatc cctttggtgt    540
ataaattaag ttttcttata ggattgctat ctatccactt ttatctaaca aaagccatta    600
tcttttcttt gcatagagag tctggtggtg taatatttca atcattttgt gattggagaa    660
acaatttcag tcattttatt gtctttatgc aattgttaga gctgtgcaga acatataggt    720
gtatatagtc aaaacattgc cttgtaattc cttcaattgc tgtctcctag caattgttat    780
tgcttcttaa gttttatatt agcaaatatt cttgttgagt tacaggaatt cccaatagct    840
tcgatttagc aaaatcatcca aaacacgaaa cttttagagc tcgagtccat aatgggattg    900
tgttgaacgt cgtaaagaag gaaaacttgg gactctcaaa tagaagccag gattcagaaa    960
attacaatga aattcctgaa tgtgttcagc ttgatagga tatggatggt agctcagcat    1020
ctgaatatgc tggggatgac gatgatgacg acaatgacaa tgacaatgac atcattactg   1080
taacaaactt ctcaaatgtg gtatctccca ttcctgttcc caaggatgat tctggggtac   1140
atgagggaca ggatcaaagt tctgtggatg gttagttttg aggaaatattt ctgttgtgtg   1200 aacaatttgg tctatctgat tcccggatca ccttaatatc aagtgccact agcaagcttg   1260
```

-continued

```
attacgtaag tagatcttaa acacctacac catttttta atcactacta cccattgcat    1320
tgaacaaact tcaagttctt cttagcttca gattaagaaa gtaccettcc ttggctttgt    1380 tgatgtggta ccattgtcca ttgtcttgtg tgtttgcaga attcctgcag ctagtggcac    1440
ttgatattaa ggtgatccgg gaatcagata gaccaaattg ttcacacaac agaaatattc    1500
ctcaaaacta accatccaca gaactttgat cctgtccctc atgtaccca gaatcatcct    1560 tgggaacagg aatgggagat accacatttg agaagtttgt tacagtaatg atgtcattgt    1620
cattgtcatt gtcgtcatca tcgtcatccc cagcatattc agatgctgag ctaccatcca    1680
tatccctatc aagctgaaca cattcaggaa tttcattgta attttctgaa tcctggcttc    1740
tatttgagag tcccaagttt tccttcttta cgacgttcaa cacaatccca ttatggagga    1800
tccactagtt ctagacggcc atgctagagt ccgcaaaaat caccagtctc tctctacaaa    1860
tctatctctc tctatttttc tccagaataa tgtgtgagta gttcccagat aagggaatta    1920
gggttcttat agggtttcgc tcatgtgttg agcatataag aaaccettag tatgtatttg    1980 tatttgtaaa atacttctat caataaaatt tctaattcct aaaaccaaaa tccagtgacc    2040
tcacgtgccg cgg                                                       2053

<210> SEQ ID NO 4
<211> LENGTH: 825
<212> TYPE: PRT
<213> ORGANISM: Arabidopsis thaliana

<400> SEQUENCE: 4

Met Asp Ile Ser Asn Glu Ala Ser Val Asp Pro Phe Ser Ile Gly Pro
1               5                   10                  15

Ser Ser Ile Met Gly Arg Thr Ile Ala Phe Arg Val Leu Phe Cys Arg
            20                  25                  30

Ser Met Ser Gln Leu Arg Arg Asp Leu Phe Arg Phe Leu Leu His Trp
        35                  40                  45

Phe Leu Arg Phe Lys Leu Thr Val Ser Pro Phe Val Ser Trp Phe His
    50                  55                  60

Pro Arg Asn Pro Gln Gly Ile Leu Ala Val Val Thr Ile Ile Ala Phe
65                  70                  75                  80

Val Leu Lys Arg Tyr Thr Asn Val Lys Ile Lys Ala Glu Met Ala Tyr
                85                  90                  95

Arg Arg Lys Phe Trp Arg Asn Met Met Arg Thr Ala Leu Thr Tyr Glu
            100                 105                 110

Glu Trp Ala His Ala Ala Lys Met Leu Glu Lys Glu Thr Pro Lys Met
        115                 120                 125

Asn Glu Ser Asp Leu Tyr Asp Glu Glu Leu Val Lys Asn Lys Leu Gln
    130                 135                 140

Glu Leu Arg His Arg Arg Gln Glu Gly Ser Leu Arg Asp Ile Met Phe
145                 150                 155                 160

Cys Met Arg Ala Asp Leu Val Arg Asn Leu Gly Asn Met Cys Asn Ser
                165                 170                 175

Glu Leu His Lys Gly Arg Leu Gln Val Pro Arg His Ile Lys Glu Tyr
            180                 185                 190

Ile Asp Glu Val Ser Thr Gln Leu Arg Met Val Cys Asn Ser Asp Ser
        195                 200                 205

Glu Glu Leu Ser Leu Glu Glu Lys Leu Ser Phe Met His Glu Thr Arg
    210                 215                 220

His Ala Phe Gly Arg Thr Ala Leu Leu Leu Ser Gly Gly Ala Ser Leu
```

```
            225                 230                 235                 240
        Gly Ala Phe His Val Gly Val Arg Thr Leu Val Glu His Lys Leu
                        245                 250                 255
        Leu Pro Arg Ile Ile Ala Gly Ser Ser Val Gly Ser Ile Ile Cys Ala
                        260                 265                 270
        Val Val Ala Ser Arg Ser Trp Pro Glu Leu Gln Ser Phe Glu Asn
                        275                 280                 285
        Ser Leu His Ser Leu Gln Phe Phe Asp Gln Leu Gly Gly Val Phe Ser
                        290                 295                 300
        Ile Val Lys Arg Val Met Thr Gln Gly Ala Leu His Asp Ile Arg Gln
        305                 310                 315                 320
        Leu Gln Cys Met Leu Arg Asn Leu Thr Ser Asn Leu Thr Phe Gln Glu
                        325                 330                 335
        Ala Tyr Asp Met Thr Gly Arg Ile Leu Gly Ile Thr Val Cys Ser Pro
                        340                 345                 350
        Arg Lys His Glu Pro Pro Arg Cys Leu Asn Tyr Leu Thr Ser Pro His
                        355                 360                 365
        Val Val Ile Trp Ser Ala Val Thr Ala Ser Cys Ala Phe Pro Gly Leu
                        370                 375                 380
        Phe Glu Ala Gln Glu Leu Met Ala Lys Asp Arg Ser Gly Glu Ile Val
        385                 390                 395                 400
        Pro Tyr His Pro Pro Phe Asn Leu Asp Pro Glu Val Gly Thr Lys Ser
                        405                 410                 415
        Ser Ser Gly Arg Arg Trp Arg Asp Gly Ser Leu Glu Val Asp Leu Pro
                        420                 425                 430
        Met Met Gln Leu Lys Glu Leu Phe Asn Val Asn His Phe Ile Val Ser
                        435                 440                 445
        Gln Ala Asn Pro His Ile Ala Pro Leu Leu Arg Leu Lys Asp Leu Val
                        450                 455                 460
        Arg Ala Tyr Gly Gly Arg Phe Ala Ala Lys Leu Ala His Leu Val Glu
        465                 470                 475                 480
        Met Glu Val Lys His Arg Cys Asn Gln Val Leu Glu Leu Gly Phe Pro
                        485                 490                 495
        Leu Gly Gly Leu Ala Lys Leu Phe Ala Gln Glu Trp Glu Gly Asp Val
                        500                 505                 510
        Thr Val Val Met Pro Ala Thr Leu Ala Gln Tyr Ser Lys Ile Ile Gln
                        515                 520                 525
        Asn Pro Thr His Val Glu Leu Gln Lys Ala Ala Asn Gln Gly Arg Arg
                        530                 535                 540
        Cys Thr Trp Glu Lys Leu Ser Ala Ile Lys Ser Asn Cys Gly Ile Glu
        545                 550                 555                 560
        Leu Ala Leu Asp Asp Ser Val Ala Ile Leu Asn His Met Arg Arg Leu
                        565                 570                 575
        Lys Lys Ser Ala Glu Arg Ala Thr Ala Thr Ser Ser Ser His His
                        580                 585                 590
        Gly Leu Ala Ser Thr Thr Arg Phe Asn Ala Ser Arg Arg Ile Pro Ser
                        595                 600                 605
        Trp Asn Val Leu Ala Arg Glu Asn Ser Thr Gly Ser Leu Asp Asp Leu
                        610                 615                 620
        Val Thr Asp Asn Asn Leu His Ala Ser Ser Gly Arg Asn Leu Ser Asp
        625                 630                 635                 640
        Ser Glu Thr Glu Ser Val Glu Leu Ser Ser Trp Thr Arg Thr Gly Gly
                        645                 650                 655
```

```
Pro Leu Met Arg Thr Ala Ser Ala Asn Lys Phe Ile Asp Phe Val Gln
        660                 665                 670

Ser Leu Asp Ile Asp Ile Ala Leu Val Arg Gly Phe Ser Ser Ser Pro
        675                 680                 685

Asn Ser Pro Ala Val Pro Pro Gly Gly Ser Phe Thr Pro Ser Pro Arg
        690                 695                 700

Ser Ile Ala Ala His Ser Asp Ile Glu Ser Asn Ser Asn Ser Asn Asn
705                 710                 715                 720

Leu Gly Thr Ser Thr Ser Ser Ile Thr Val Thr Glu Gly Asp Leu Leu
            725                 730                 735

Gln Pro Glu Arg Thr Ser Asn Gly Phe Val Leu Asn Val Val Lys Arg
        740                 745                 750

Glu Asn Leu Gly Met Pro Ser Ile Gly Asn Gln Asn Thr Glu Leu Pro
        755                 760                 765

Glu Ser Val Gln Leu Asp Ile Pro Glu Lys Glu Met Asp Cys Ser Ser
        770                 775                 780

Val Ser Glu His Glu Glu Asp Asp Asn Asp Asn Glu Glu Glu His Asn
785                 790                 795                 800

Gly Ser Ser Leu Val Thr Val Ser Ser Glu Asp Ser Gly Leu Gln Glu
            805                 810                 815

Pro Val Ser Gly Ser Val Ile Asp Ala
        820                 825

<210> SEQ ID NO 5
<211> LENGTH: 4
<212> TYPE: PRT
<213> ORGANISM: Artificial Sequence
<220> FEATURE:
<223> OTHER INFORMATION: peptide motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

Arg Xaa Xaa Leu
1

<210> SEQ ID NO 6
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 6

Gly Xaa Gly Xaa Xaa Gly
1               5

<210> SEQ ID NO 7
<211> LENGTH: 5
<212> TYPE: PRT
<213> ORGANISM: Artificial Sequence
<220> FEATURE:
<223> OTHER INFORMATION: peptide motif
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

Gly Xaa Ser Xaa Gly
1               5

<210> SEQ ID NO 8
<211> LENGTH: 34
<212> TYPE: DNA
<213> ORGANISM: Artificial Sequence
<220> FEATURE:
<223> OTHER INFORMATION: primer sequence

<400> SEQUENCE: 8
cacctacatc cagtagattg cacgtcacac acta                                    34

<210> SEQ ID NO 9
<211> LENGTH: 32
<212> TYPE: DNA
<213> ORGANISM: Artificial Sequence
<220> FEATURE:
<223> OTHER INFORMATION: primer sequence

<400> SEQUENCE: 9
ctctaaaagt ttcgtgtttt ggatgatttg ct                                      32

<210> SEQ ID NO 10
<211> LENGTH: 35
<212> TYPE: DNA
<213> ORGANISM: Artificial Sequence
<220> FEATURE:
<223> OTHER INFORMATION: primer sequence

<400> SEQUENCE: 10
ttggtcgaca tggatataag taatgaggcc aatgt                                   35

<210> SEQ ID NO 11
<211> LENGTH: 35
<212> TYPE: DNA
<213> ORGANISM: Artificial Sequence
<220> FEATURE:
<223> OTHER INFORMATION: primer sequence

<400> SEQUENCE: 11
attgctagca ccatccacag aactttgatc ctgtc                                   35

<210> SEQ ID NO 12
<211> LENGTH: 37
<212> TYPE: DNA
<213> ORGANISM: Artificial Sequence
<220> FEATURE:
<223> OTHER INFORMATION: primer sequence

<400> SEQUENCE: 12
atactcgagt ccataatggg attgtgttga acgtcgt                                 37

<210> SEQ ID NO 13
<211> LENGTH: 36
<212> TYPE: DNA
<213> ORGANISM: Artificial Sequence
```

<220> FEATURE:
<223> OTHER INFORMATION: primer sequence

<400> SEQUENCE: 13
tcgaagcttg ctagtggcac ttgatattaa ggtgat        36

<210> SEQ ID NO 14
<211> LENGTH: 37
<212> TYPE: DNA
<213> ORGANISM: Artificial Sequence
<220> FEATURE:
<223> OTHER INFORMATION: primer sequence

<400> SEQUENCE: 14
ataggatcct ccataatggg attgtgttga acgtcgt        37

<210> SEQ ID NO 15
<211> LENGTH: 34
<212> TYPE: DNA
<213> ORGANISM: Artificial Sequence
<220> FEATURE:
<223> OTHER INFORMATION: primer sequence

<400> SEQUENCE: 15
tctttctgca gctagtggca cttgatatta aggt        34

<210> SEQ ID NO 16
<211> LENGTH: 36
<212> TYPE: DNA
<213> ORGANISM: Artificial Sequence
<220> FEATURE:
<223> OTHER INFORMATION: primer sequence

<400> SEQUENCE: 16
tatgggccct acatccagta gattgcacgt cacaca        36

<210> SEQ ID NO 17
<211> LENGTH: 38
<212> TYPE: DNA
<213> ORGANISM: Artificial Sequence
<220> FEATURE:
<223> OTHER INFORMATION: primer sequence

<400> SEQUENCE: 17
atgctcgagc tctaaaagtt tcgtgttttg gatgattt        38

<210> SEQ ID NO 18
<211> LENGTH: 30
<212> TYPE: DNA
<213> ORGANISM: Artificial Sequence
<220> FEATURE:
<223> OTHER INFORMATION: primer sequence

<400> SEQUENCE: 18
acttctagac ggccatgcta gagtccgcaa        30

<210> SEQ ID NO 19
<211> LENGTH: 30
<212> TYPE: DNA
<213> ORGANISM: Artificial Sequence
<220> FEATURE:
<223> OTHER INFORMATION: primer sequence

<400> SEQUENCE: 19
ttaccgcggc acgtgaggtc actggatttt        30

<210> SEQ ID NO 20
<211> LENGTH: 27
<212> TYPE: DNA
<213> ORGANISM: Artificial Sequence
<220> FEATURE:
<223> OTHER INFORMATION: primer sequence

<400> SEQUENCE: 20
aaaaagcctg aactcaccgc gacgtct                                27

<210> SEQ ID NO 21
<211> LENGTH: 24
<212> TYPE: DNA
<213> ORGANISM: Artificial Sequence
<220> FEATURE:
<223> OTHER INFORMATION: primer sequence

<400> SEQUENCE: 21
tacttctaca cagccatcgg tcca                                   24

<210> SEQ ID NO 22
<211> LENGTH: 23
<212> TYPE: DNA
<213> ORGANISM: Artificial Sequence
<220> FEATURE:
<223> OTHER INFORMATION: primer sequence

<400> SEQUENCE: 22
ctgaattgtc gaggtcgaag atc                                    23

<210> SEQ ID NO 23
<211> LENGTH: 21
<212> TYPE: DNA
<213> ORGANISM: Artificial Sequence
<220> FEATURE:
<223> OTHER INFORMATION: primer sequence

<400> SEQUENCE: 23
agcagccaaa tgggtctgtc c                                      21

<210> SEQ ID NO 24
<211> LENGTH: 24
<212> TYPE: DNA
<213> ORGANISM: Artificial Sequence
<220> FEATURE:
<223> OTHER INFORMATION: primer sequence

<400> SEQUENCE: 24
cttctcatta tcggtggtga acat                                   24

<210> SEQ ID NO 25
<211> LENGTH: 21
<212> TYPE: DNA
<213> ORGANISM: Artificial Sequence
<220> FEATURE:
<223> OTHER INFORMATION: primer sequence

<400> SEQUENCE: 25
ctctgtctgg attggagggt c                                      21

<210> SEQ ID NO 26
<211> LENGTH: 20
<212> TYPE: DNA
<213> ORGANISM: Artificial Sequence
<220> FEATURE:
<223> OTHER INFORMATION: primer sequence

```
<400> SEQUENCE: 26
gcttgagaaa tggtcggaaa                                                    20

<210> SEQ ID NO 27
<211> LENGTH: 26
<212> TYPE: DNA
<213> ORGANISM: Artificial Sequence
<220> FEATURE:
<223> OTHER INFORMATION: primer sequence

<400> SEQUENCE: 27
tgccgctata accgttttct cttgga                                             26

<210> SEQ ID NO 28
<211> LENGTH: 27
<212> TYPE: DNA
<213> ORGANISM: Artificial Sequence
<220> FEATURE:
<223> OTHER INFORMATION: primer sequence

<400> SEQUENCE: 28
atgttcccca ccagtatgtt gctgtcc                                            27

<210> SEQ ID NO 29
<211> LENGTH: 23
<212> TYPE: DNA
<213> ORGANISM: Artificial Sequence
<220> FEATURE:
<223> OTHER INFORMATION: primer sequence

<400> SEQUENCE: 29
atgcggttgg ctacgcagga caa                                                23

<210> SEQ ID NO 30
<211> LENGTH: 23
<212> TYPE: DNA
<213> ORGANISM: Artificial Sequence
<220> FEATURE:
<223> OTHER INFORMATION: primer sequence

<400> SEQUENCE: 30
tcatgcagcc gtcgtcctcc cct                                                23

<210> SEQ ID NO 31
<211> LENGTH: 24
<212> TYPE: DNA
<213> ORGANISM: Artificial Sequence
<220> FEATURE:
<223> OTHER INFORMATION: primer sequence

<400> SEQUENCE: 31
tggaatagcc gccattaccg cctt                                               24

<210> SEQ ID NO 32
<211> LENGTH: 28
<212> TYPE: DNA
<213> ORGANISM: Artificial Sequence
<220> FEATURE:
<223> OTHER INFORMATION: primer sequence

<400> SEQUENCE: 32
agaaacttgt tggtgttgga ctccaatg                                           28

<210> SEQ ID NO 33
```

```
<211> LENGTH: 20
<212> TYPE: DNA
<213> ORGANISM: Artificial Sequence
<220> FEATURE:
<223> OTHER INFORMATION: primer sequence

<400> SEQUENCE: 33
atgccatcga ttgggaacca                                            20

<210> SEQ ID NO 34
<211> LENGTH: 23
<212> TYPE: DNA
<213> ORGANISM: Artificial Sequence
<220> FEATURE:
<223> OTHER INFORMATION: primer sequence

<400> SEQUENCE: 34
caccggttct tgtaaaccgg aat                                        23

<210> SEQ ID NO 35
<211> LENGTH: 24
<212> TYPE: DNA
<213> ORGANISM: Artificial Sequence
<220> FEATURE:
<223> OTHER INFORMATION: primer sequence

<400> SEQUENCE: 35
gaggctggat ctggcaaaca cgtt                                       24

<210> SEQ ID NO 36
<211> LENGTH: 25
<212> TYPE: DNA
<213> ORGANISM: Artificial Sequence
<220> FEATURE:
<223> OTHER INFORMATION: primer sequence

<400> SEQUENCE: 36
tgtgtaatga cctctagcaa aatta                                      25

<210> SEQ ID NO 37
<211> LENGTH: 26
<212> TYPE: DNA
<213> ORGANISM: Artificial Sequence
<220> FEATURE:
<223> OTHER INFORMATION: primer sequence

<400> SEQUENCE: 37
cataatggga ttgtgttgaa cgtcgt                                     26

<210> SEQ ID NO 38
<211> LENGTH: 24
<212> TYPE: DNA
<213> ORGANISM: Artificial Sequence
<220> FEATURE:
<223> OTHER INFORMATION: primer sequence

<400> SEQUENCE: 38
gtcatcatcg tcatccccag cata                                       24

<210> SEQ ID NO 39
<211> LENGTH: 25
<212> TYPE: DNA
<213> ORGANISM: Artificial Sequence
<220> FEATURE:
<223> OTHER INFORMATION: primer sequence

<400> SEQUENCE: 39
```
cctcagcctc tctcttactt ggctt    25

<210> SEQ ID NO 40
<211> LENGTH: 21
<212> TYPE: DNA
<213> ORGANISM: Artificial Sequence
<220> FEATURE:
<223> OTHER INFORMATION: primer sequence

<400> SEQUENCE: 40
ccaggagaag taagggacga g    21

<210> SEQ ID NO 41
<211> LENGTH: 27
<212> TYPE: DNA
<213> ORGANISM: Artificial Sequence
<220> FEATURE:
<223> OTHER INFORMATION: primer sequence

<400> SEQUENCE: 41
ctacttgttg gtccataatg ttcgtca    27

<210> SEQ ID NO 42
<211> LENGTH: 24
<212> TYPE: DNA
<213> ORGANISM: Artificial Sequence
<220> FEATURE:
<223> OTHER INFORMATION: primer sequence

<400> SEQUENCE: 42
cgtagataac tccattcctt gcct    24

<210> SEQ ID NO 43
<211> LENGTH: 28
<212> TYPE: DNA
<213> ORGANISM: Artificial Sequence
<220> FEATURE:
<223> OTHER INFORMATION: primer sequence

<400> SEQUENCE: 43
gtcttaacca actttttcaa cctctgtt    28

<210> SEQ ID NO 44
<211> LENGTH: 29
<212> TYPE: DNA
<213> ORGANISM: Artificial Sequence
<220> FEATURE:
<223> OTHER INFORMATION: primer sequence

<400> SEQUENCE: 44
ccaaaccgaa aacagtgaaa gcaaagagt    29

<210> SEQ ID NO 45
<211> LENGTH: 24
<212> TYPE: DNA
<213> ORGANISM: Artificial Sequence
<220> FEATURE:
<223> OTHER INFORMATION: primer sequence

<400> SEQUENCE: 45
aatctatcct tcaacctccg ccgt    24

<210> SEQ ID NO 46
<211> LENGTH: 24
<212> TYPE: DNA

```
<213> ORGANISM: Artificial Sequence
<220> FEATURE:
<223> OTHER INFORMATION: primer sequence

<400> SEQUENCE: 46
agagaatctg ctccaaggtc agct                                          24

<210> SEQ ID NO 47
<211> LENGTH: 24
<212> TYPE: DNA
<213> ORGANISM: Artificial Sequence
<220> FEATURE:
<223> OTHER INFORMATION: primer sequence

<400> SEQUENCE: 47
ggatctcctt tccctccgat gttt                                          24

<210> SEQ ID NO 48
<211> LENGTH: 24
<212> TYPE: DNA
<213> ORGANISM: Artificial Sequence
<220> FEATURE:
<223> OTHER INFORMATION: primer sequence

<400> SEQUENCE: 48
ataaattcag agagctcggc gggt                                          24

<210> SEQ ID NO 49
<211> LENGTH: 23
<212> TYPE: DNA
<213> ORGANISM: Artificial Sequence
<220> FEATURE:
<223> OTHER INFORMATION: primer sequence

<400> SEQUENCE: 49
tggcatcact ggtctcccga tgt                                           23

<210> SEQ ID NO 50
<211> LENGTH: 27
<212> TYPE: DNA
<213> ORGANISM: Artificial Sequence
<220> FEATURE:
<223> OTHER INFORMATION: primer sequence

<400> SEQUENCE: 50
tcatacctct tgatttcagt aacgaga                                       27

<210> SEQ ID NO 51
<211> LENGTH: 25
<212> TYPE: DNA
<213> ORGANISM: Artificial Sequence
<220> FEATURE:
<223> OTHER INFORMATION: primer sequence

<400> SEQUENCE: 51
agtcactatc gtccttccgg cacaa                                         25

<210> SEQ ID NO 52
<211> LENGTH: 26
<212> TYPE: DNA
<213> ORGANISM: Artificial Sequence
<220> FEATURE:
<223> OTHER INFORMATION: primer sequence

<400> SEQUENCE: 52
cgctctgtac gattgctatt tcctct                                        26
```

```
<210> SEQ ID NO 53
<211> LENGTH: 26
<212> TYPE: DNA
<213> ORGANISM: Artificial Sequence
<220> FEATURE:
<223> OTHER INFORMATION: primer sequence

<400> SEQUENCE: 53
tcaagtcagt tcactgcaga tctaat                                        26

<210> SEQ ID NO 54
<211> LENGTH: 28
<212> TYPE: DNA
<213> ORGANISM: Artificial Sequence
<220> FEATURE:
<223> OTHER INFORMATION: primer sequence

<400> SEQUENCE: 54
caactcggta agaccaggc atagtgaa                                       28

<210> SEQ ID NO 55
<211> LENGTH: 22
<212> TYPE: DNA
<213> ORGANISM: Artificial Sequence
<220> FEATURE:
<223> OTHER INFORMATION: primer sequence

<400> SEQUENCE: 55
tcgcaaaaca cacatcacac ac                                            22

<210> SEQ ID NO 56
<211> LENGTH: 23
<212> TYPE: DNA
<213> ORGANISM: Artificial Sequence
<220> FEATURE:
<223> OTHER INFORMATION: primer sequence

<400> SEQUENCE: 56
gtgattgacg atttgatggt aag                                           23

<210> SEQ ID NO 57
<211> LENGTH: 19
<212> TYPE: DNA
<213> ORGANISM: Artificial Sequence
<220> FEATURE:
<223> OTHER INFORMATION: primer sequence

<400> SEQUENCE: 57
tggtcttcct gcttctgcc                                                19

<210> SEQ ID NO 58
<211> LENGTH: 19
<212> TYPE: DNA
<213> ORGANISM: Artificial Sequence
<220> FEATURE:
<223> OTHER INFORMATION: primer sequence

<400> SEQUENCE: 58
ccgcttctca ctgcctcat                                                19
```

GENE SILENCING OF SUGAR-DEPENDENT 1 IN *JATROPHA CURCAS*

CROSS-REFERENCE TO RELATED APPLICATIONS

The present application is a national stage filing under 35 U.S.C. §371 of PCT/SG2014/000082, filed on 25 Feb. 2014, and is related to and claims priority to U.S. Provisional Patent Application Ser. No. 61/773,386, filed 6 Mar. 2013. Each application is incorporated herein by reference.

SEQUENCE SUBMISSION

The present application is being filed along with a Sequence Listing in electronic format. The Sequence Listing is entitled 2577229PCTSequencListing.txt, was created on 18 Feb. 2014 and is 43 kb in size. The information in the electronic format of the Sequence Listing is part of the present application and is incorporated herein by reference in its entirety.

BACKGROUND OF THE INVENTION

The present invention relates to the field of plant molecular biology and gene silencing. More particularly, the present invention relates to gene silencing of Sugar-dependent 1 (JcSDP1) in *Jatropha curcas*. JcSDP1 encodes a patatin-domain triacylglyerol lipase. Silencing of JcSDP1 enhances seed oil accumulation in *J. curcas*.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The diminishing stock of fossil fuel has catalyzed a soaring demand for renewable energy sources world-wide. To meet this demand active research has been initiated relating to solar, wind, tidal and geothermal power generations during the last several decades. Likewise, there is also an increasing focus on biofuels, which are energy sources derived from renewable biomass. There are two main types of biofuels: bioethanol and biodiesel, which are generally used as gasoline and diesel additives, respectively. Bioethanol is mainly produced by fermentation using sugar or starch derived from crops such as sugar cane and corn. Biodiesel, on the other hand, is obtained by trans-esterification of plant oils and animal fats. In 2010, the global biofuel production reached 105 billion liters and provided 2.7% of the world's energy needs for transportation. It has been forecast that biofuel may account for more than a quarter of the world's demand for transportation fuels by 2050 (1).

Biodiesel is generally produced from oil seed crops such as rape in temperate countries and oil palm in the tropics. In the past several years, a small tree called *Jatropha curcus* grown in the tropical and subtropical regions has emerged as an attractive candidate crop for biodiesel production. *Jatropha* has several interesting attributes making it suitable for consideration as a biodiesel plant. *Jatropha* seeds contain up to 40% oil consisting of approximately 75% unsaturated fatty acids (2, 3), with a high level (around 47%) of linoleic acid (C18:2) (4). In addition to having a high oil content and favorable oil composition for biodiesel, *Jatropha* plants have a short gestation period and adapt well to a wide range of agro-climatic conditions (5, 6). Moreover, its ability to grow on marginal land reduces the possibility that *Jatropha* may compete with food crops for arable land.

Because of *Jatropha* has just been recently been domesticated much work remains to be done to improve its agronomic traits either by traditional breeding or by gene technology.

Given the commercial interest in *Jatropha* seed oil, it is not surprising that the immediate focus is on seed oil content and quality. With respect to the latter trait, Qu et al. (7) have recently reported that gene silencing of JcFAD2 can greatly enhance the proportion of oleic acids in seeds of transgenic *Jatropha*. Here, we addressed the issue of increasing levels of oil accumulation in *Jatropha* seeds by genetic modification.

Plant oil in seeds is stored as triacylglycerol (TAG) consisting of three fatty acid chains (usually C16 or C18) covalently linked to glycerol. Depending on the plant source, TAGs may contain fatty acids of different chain lengths and degree of saturation and the fatty acids may be decorated with diverse modifications. Plant TAGs are generally stored in small organelles called oil bodies which are assembled in developing seeds, flower petals, pollen grains and fruits of a huge number of plant species (8, 9). During seed germination TAGs are hydrolyzed into fatty acids and glycerol and this reaction is catalyzed by TAG lipases, which are widely distributed in plants but also found in animals and microorganisms (10). Among the known lipases, the unorthodox patatin-like TAG lipases (PTLs) are oil body-associated enzymes that play a major role in the initiation of TAG degradation in yeast, mammals and insects (11, 12). During seed germination, TAG lipases initiate TAG degradation into glycerol and free fatty acids and the released fatty acids are consumed through the beta-oxidation pathway which releases energy for early seedling growth (13, 14).

Recently, Eastmond (15, 16) has shown that the sugar-dependent 1 (SDP1) of *Arabidopsis* encodes a patatin-like acyl hydrolase domain. The encoded protein, SDP1, is specifically responsible for the first step of TAG degradation during *Arabidopsis* seed germination. This enzyme is also able to associate with oil body surface as well as the other reported PTLs. A T-DNA insertion SDP1 mutant allele, sdp1-5, displayed growth retardation on a sugar-deficient medium due to the deficiency of glycerol and free fatty acids, which are products of TAG degradation (15, 16). The study of Eastmond (15, 16) showed an accumulation of clustered oil bodies in seedling cotyledons and a higher TAG levels in sdp1-5 than WT (Col-0).

It is desired to increase seed oil content in *Jatropha* which would be an important agronomic trait for this biodiesel crop.

SUMMARY OF THE INVENTION

The present invention relates to the field of plant molecular biology and gene silencing. More particularly, the present invention relates to gene silencing of Sugar-dependent 1 (JcSDP1) in *Jatropha curcas*. JcSDP1 encodes a patatin-domain triacylglyerol lipase. Silencing of JcSDP1 enhances seed oil accumulation in *J. curcas*.

Thus, in one aspect, the present invention provides for In a first aspect, the present invention provides an isolated nucleic acid encoding a JcSDP1 protein comprising the amino acid sequence set forth in SEQ ID NO:2. In one embodiment, the nucleic acid comprises the nucleotide sequence set forth in SEQ ID NO:1. In another embodiment, the nucleic acid comprises the nucleotide sequence set forth as nucleotides 874-3450 of SEQ ID NO:1. In an additional embodiment, the nucleic acid comprises the nucleotide sequence set forth as nucleotides 874-3447 of SEQ ID NO:1. In a further embodiment, the nucleic acid further comprises a plant operable promoter operably linked to a nucleic acid comprising the coding sequence, or a nucleic acid comprising the 5' UTR (or portion thereof) and the coding sequence, or a nucleic acid comprising the coding sequence and the 3' UTR (or portion thereof) or a nucleic acid comprising the 5' UTR (or portion thereof), coding sequence and the 3' UTR (or portion thereof. In one embodiment, the promoter is a seed specific promoter. In another embodiment, the seed specific promoter is a Jatropha seed specific promoter. In a further embodiment, the Jatropha seed specific promoter is the JcSDP1 promoter. In one embodiment, the JcSDP1 promoter comprises nucleotides 1-722 of SEQ ID NO:1. In another embodiment, functional fragments of the JcSDP1 promoter can be used.

In a second aspect, the present invention provides a construct or vector comprising an isolated nucleic acid as described herein. In one embodiment, the construct or vector is an expression construct or vector. In another embodiment, the construct or vector further comprises a selectable marker. In a further embodiment, the construct or vector comprises a Cre-lox recombination marker free system.

In a third aspect, the present invention provides a transgenic plant comprising a nucleic acid or vector described herein. In one embodiment, the transgenic plant is a Jatropha plant.

In a fourth aspect, the present invention provides for the down regulation of a Jatropha SDP1 gene. In one embodiment, the down regulation of a Jatropha SDP1 gene involves using RNA interference (RNAi), including double stranded RNA, siRNA, microRNA, and hairpin RNA. In another embodiment, the down regulation of a Jatropha SDP1 gene involves using viral induced gene silencing (VIGS). In one embodiment, a nucleic acid is provided which down regulates the Jatropha SDP1 gene. In another embodiment, a nucleic acid is provided which down regulates the Jatropha curcas SDP1 gene. In some embodiments, the nucleic acid comprises nucleotides 3161 to 3533 of SEQ ID NO:1. In another embodiment, a suitable nucleic acid for use in down regulating the Jatropha SDP1 gene is selected using well known RNAi considerations and algorithms. In some embodiments, the nucleic acid further comprises a plant operable promoter operably linked to the nucleic acid. In one embodiment, the promoter is a seed specific promoter. In another embodiment, the seed specific promoter is a Jatropha seed promoter. In a further embodiment, the Jatropha seed specific promoter is the JcSDP1 promoter. In one embodiment, the JcSDP1 promoter comprises nucleotides 1-722 of SEQ ID NO:1. In another embodiment, functional fragments of the JcSDP1 promoter can be used. In an additional embodiment, the promoter comprises the JcSDP1 promoter and the 3' UTR (or portion thereof). In one embodiment, a nucleic acid suitable for down regulating Jatropha SDP1 gene is set forth in SEQ ID NO:3. According to this aspect, the present invention also provides a vector comprising an isolated nucleic acid as described herein. In one embodiment, the vector is an expression vector. In another embodiment, the vector further comprises a selectable marker. In a further embodiment, the vector comprises a Cre-lox recombination marker free system. According to this aspect, the present invention further provides a transgenic or infected plant or plant cell comprising a nucleic acid or vector described herein. In one embodiment, the transgenic or infected plant or plant cell is a Jatropha plant or plant cell. In some embodiments, the down regulation of a Jatropha SDP1 gene provides enhanced seed oil accumulation in a transgenic or infected Jatropha plant, such as Jatropha curcas.

In a fifth aspect, the present invention provides methods of increasing seed oil accumulation in Jatropha, such as Jatropha curcas. In one embodiment, a method involves modulating the level of activity of a Sugar-dependent 1 (SDP1) gene, such as JcSDP1 gene, which encodes a patatin-domain triacylglycerol lipase in the host Jatropha cell or Jatropha plant. The level of activity of the lipase can be reduced by reducing expression of the SDP1 gene. In one embodiment, the modulation of the level of activity of the lipase is a reduction in the activity of the lipase. The level of activity of the lipase can be reduced by using RNAi techniques described herein in which the lipase is the target for the RNAi. Alternatively, the level of activity of the lipase can be reduced using VIGS techniques as described herein in which at least a partial fragment of the target gene is used. In one embodiment, Jatropha RNAi plants accumulate about 13% to about 30% higher seed oil than control plants.

BRIEF DESCRIPTION OF THE DRAWINGS

FIG. 1A: Scanning electron microscopy (SEM) showing the seed surface structure of WT (Col-0) and sdp1-5. FIG. 1B: Comparative dry seed weight of WT (Col-0) and sdp1-5. FIG. 1C: Total amount of fatty acids per seed of WT (Col-0) and sdp1-5. FIG. 1D: Relative fatty acids of dried seeds of WT (Col-0) and sdp1-5. FIG. 1E: Fatty acid profiles of WT (Col-0) and sdp1-5 seeds. FIG. 1F: Seed eicosenoic acid (20:1) content. FIG. 1G: TLC separation of neutral lipid fractions from WT (Col-0) and three lines of sdp1-5 null mutant. 300 µg of neutral lipids were fractionated by TLC on silica gel plates. TAG, Triacylglycerol (Triolein, Sigma T7140); FFA, Free Fatty Acid (Oleic acid, Sigma 75090), Mix, mix TAG and FFA, SE, sterol ester; FFA, free fatty acid; DAG, diacylglycerol. H) Profiling of relative amounts of FFA and TAG by GC/MS. The absolute amount was calculated using the C15:0 as an internal control by comparing their peak areas. *P<0.05 or **P<0.01 versus WT (Col-0). Each experiment was performed with 100 seeds per line with 5 biological replicates. Error bar shows SD, standard deviation (n=5). DW, Dry weight FIG. 2A: TEM analysis of oil body distribution in WT (Col-0) and sdp1-5 mature seeds. The scale bar is 5 µm. PSV; protein storage vacuole, CW; cell wall, OB; oil body. FIG. 2B: Numbers of oil bodies per cell in mature seeds of WT (Col-0) and sdp1-5. A cell has an average of 196 µm² cross-sectional area (Mean value with SD; n=5). FIG. 2C: Expression levels of AtOLE1 (At4g25140), AtOLE2 (At5g40420), and AtOLE3 (At5g51210) in early developing stages of seeds (3 to 5 DAP) from WT (Col-0) and sdp1-5. Actin1 (At2g37620) was used as an internal control. *P<0.05, P<0.01, or *P<0.001 versus WT (Col-0). There were 5 biological replicates. SD, standard deviation (n=5). DAP: Day after pollination.

FIGS. 3A and 3B show cloning of JcSDP1 gene from Jatropha plants and complementation of the Arabidopsis sdp1-5 mutant. FIG. 3A: Deduced amino acid sequence of JcSDP1 (SEQ ID NO:2) and alignment to the AtSDP1 amino acid sequence (SEQ ID NO:4). Bold line; patatin domain, star (*****); site-1 protease (S1P) target sequence, RXXL (SEQ ID NO:5), GXGXXG (SEQ ID NO:6); oxyanion hole motif, GXSXG (SEQ ID NO:7); lipase consensus motif with catalytic serine. FIG. 3B: Complementation of sdp1-5 with JcSDP1. WT (Col-0), sdp1-5, and CaMV35S: JcSDP1/sdp1-5 transgenic plants were grown on MS medium with or without sucrose (1%).

FIG. 4A: Composition of putative cis-elements in JcSDP1 promoter. FIG. 4B: Transient ProJcSDP1:GUS expression in *Jatropha* fruit and leaf. FIG. 4C: Heterologous expressions of ProJcSDP1:GUS in transgenic *Arabidopsis* plants. a) 14 day-old seedling, b-c) inflorescence, d-e) rosette leaf, f) siliques, g) seeds at different developing stages, h) young seeds (3 to 4 DAP, globular-stage embryo), i) mid-stage seeds (9 to 10 DAP, mature green embryo). DAP: Days after pollination. FIG. 4D: Sugar-dependent expression of ProJcSDP1:GUS transgenic plants (14 day-old seedling). 1% or 3% fructose, glucose, and sucrose were used as a sugar source and mannitol was used as a control for osmotic stress. FIG. 4E: JcSDP1 gene expression profiles using quantitative real-time PCR at different seed developing stages (S1; 1WAF, S2; 2 to 3WAF, S3; 4 to 6WAF, and S4; 7 to 8WAF, WAF: weeks after fertilization JcTubulin expression levels were used as an internal control. Mean values are given with SD (n=3).

FIGS. 5A-5E show construction of ProJcSDP1:JcSDP1-RNAi transgenic *Jatropha* plants and analysis of seed oils. FIG. 5A: Structure of the inducible ProJcSDP:SDP1-RNAi marker-free construction. FIG. 5B: ProJcSDP:SDP1-RNAi marker-free transgenic plants; a-c) T1 generation of dried seeds. d) Overall phenotype of T1 transgenic plants generated from T1 embryos. e) Size comparison of the 5$^{th}$ leaf between control (CK) plants and JcSDP1-RNAi transgenic line #158. FIG. 5C: Total fatty acid analysis in mature endosperm of T1 seed. FIG. 5D: Fatty acid profile in JcSDP1-RNAi transgenic lines. FIG. 5E: JcSDP1 transcript levels in transgenic lines. JcTubulin expression levels were used as an internal control. Numbers refer to transgenic line numbers. Asterisks indicated statistically significant difference compared with the control, *$P<0.05$, $P<0.01$, or *$P<0.001$ versus CK, in different biological replicates. CK, 35S:GFP control.

FIG. 6A: The T-DNA is inserted in the first exon of SDP1 resulting in a null mutation. FIG. 6B: Isolation of the homozygous sdp1-5 mutant by RT-PCR. FIG. 6C: Expression levels of AtSDP1 in early developing seeds (3 to 5 DAP). Actin1 (At2g37620) expression levels were used as an internal control. *$P<0.05$, $P<0.01$, or *$P<0.001$ versus Col-0 for 5 biological replicates. SD, standard deviation (n=5). DAP: Days after pollination.

FIG. 8A: Total lipids were extracted from mature endosperm of CK and JcSDP1-RNAi transgenic line #158 and 300 µg of total neutral lipids were separated by TLC on silica gel plate and stained with Iodine ($I_2$). SE, sterol ester; TAG, triacylglycerol; FFA, free fatty acid; DAG, diacylglycerol. FIG. 8B: Profiling of relative amounts of FFA and TAG by GC/MS. The absolute amount was calculated using the C15:0 as an internal control by comparing their peak areas.

FIG. 10A: Total genomic DNA were digested with XhoI restriction enzyme and hybridized with HPT probe. FIG. 10B: Total lipid content (%, w/w) in individual transgenic line carrying the JcSDP1-RNAi construct.

DETAILED DESCRIPTION OF THE INVENTION

Figure 1:
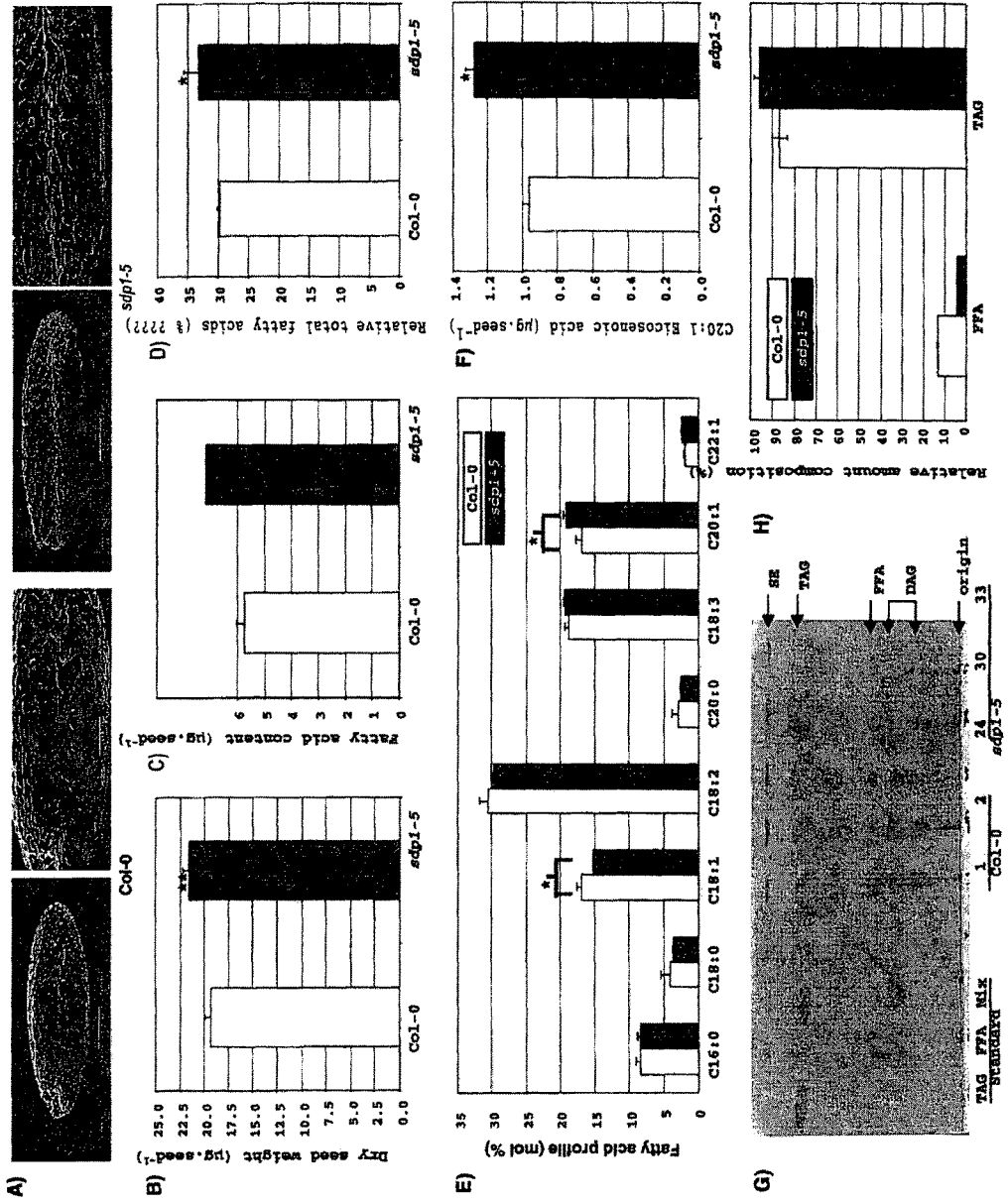
FIGS. 1A-1G show sdp1-5 mutant accumulates a higher TAG levels than WT (Col-0) in mature seeds.

The present invention relates to the field of plant molecular biology and gene silencing. More particularly, the present invention relates to gene silencing of Sugar-dependent 1 (JcSDP1) in *Jatropha curcas*. JcSDP1 encodes a patatin-domain triacylglyerol lipase. Silencing of JcSDP1 enhances seed oil accumulation in *J. curcas*.

Unless defined otherwise, all technical and scientific terms used herein have the same meaning as is commonly understood by one of skill in the art to which the invention belongs.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

As used herein, "phenotype" refers to the detectable characteristics of a cell or organism, which characteristics are the manifestation of gene expression.

The terms "polynucleotide," nucleic acid" and "nucleic acid molecule are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers Amino acids may be referred to by their commonly known three-letter or one-letter symbols. Amino acid sequences are written left to right in amino to carboxy orientation, respectively. Numeric ranges are inclusive of the numbers defining the range.

Thus, in one aspect, the present invention provides for In a first aspect, the present invention provides an isolated nucleic acid encoding a JcSDP1 protein comprising the amino acid sequence set forth in SEQ ID NO:2. In one embodiment, the nucleic acid comprises the nucleotide sequence set forth in SEQ ID NO: 1. In another embodiment, the nucleic acid comprises the nucleotide sequence set forth as nucleotides 874-3450 of SEQ ID NO: 1. In an additional embodiment, the nucleic acid comprises the nucleotide sequence set forth as nucleotides 874-3447 of SEQ ID NO: 1. In a further embodiment, the nucleic acid further comprises a plant operable promoter operably linked to a nucleic acid comprising the coding sequence, or a nucleic acid comprising the 5' UTR (or portion thereof) and the coding sequence, or a nucleic acid comprising the coding sequence and the 3' UTR (or portion thereof) or a nucleic acid comprising the 5' UTR (or portion thereof), coding sequence and the 3' UTR (or portion thereof. In another embodiment, the seed specific promoter is a *Jatropha* seed specific promoter. In a further embodiment, the *Jatropha* seed specific promoter is the JcSDP1 promoter. In one embodiment, the JcSDP1 promoter comprises nucleotides 1-722 of SEQ ID NO:1. In another embodiment, functional fragments of the JcSDP1 promoter can be used. Useful functional fragments of the JcSDP1 promoter can be identified by the skilled artisan using conventional techniques well known in the art including, but not limited to promoter analysis software, promoter cis-element software and the like.

In a second aspect, the present invention provides a construct or vector comprising an isolated nucleic acid as described herein. In one embodiment, the construct or vector is an expression construct or vector. In another embodiment, the construct or vector further comprises a selectable marker. In a further embodiment, the construct or vector comprises a Cre-lox recombination marker free system.

In a third aspect, the present invention provides a transgenic plant comprising a nucleic acid or vector described herein. In one embodiment, the transgenic plant is a *Jatropha* plant.

In a fourth aspect, the present invention provides for the down regulation of a *Jatropha* SDP1 gene. In one embodiment, the down regulation of a *Jatropha* SDP1 gene involves using RNA interference (RNAi), including double stranded RNA, siRNA, microRNA, and hairpin RNA. In another embodiment, the down regulation of a *Jatropha* SDP1 gene involves using viral induced gene silencing (VIGS). In one embodiment, a nucleic acid is provided which down regulates the *Jatropha* SDP1 gene. In another embodiment, a nucleic acid is provided which down regulates the *Jatropha curcas* SDP1 gene. In some embodiments, the nucleic acid comprises nucleotides 3161 to 3533 of SEQ ID NO:1. In another embodiment, a suitable nucleic acid for use in down regulating the *Jatropha* SDP1 gene is selected using well known RNAi considerations and algorithms. In some embodiments, the nucleic acid further comprises a plant operable promoter operably linked to the nucleic acid. In one embodiment, the promoter is a seed specific promoter. In another embodiment, the seed specific promoter is a *Jatropha* seed promoter. In a further embodiment, the *Jatropha* seed specific promoter is the JcSDP1 promoter. In one embodiment, the JcSDP1 promoter comprises nucleotides 1-722 of SEQ ID NO: 1. In another embodiment, functional fragments of the JcSDP1 promoter can be used.

In an additional embodiment, the promoter comprises the JcSDP1 promoter and the 3' UTR (or portion thereof). In one embodiment, a nucleic acid suitable for down regulating *Jatropha* SDP1 gene is set forth in SEQ ID NO:3. According to this aspect, the present invention also provides a vector comprising an isolated nucleic acid as described herein. In one embodiment, the vector is an expression vector. In another embodiment, the vector further comprises a selectable marker. In a further embodiment, the vector comprises a Cre-lox recombination marker free system. According to this aspect, the present invention further provides a transgenic or infected plant or plant cell comprising a nucleic acid or vector described herein. In one embodiment, the transgenic or infected plant or plant cell is a *Jatropha* plant or plant cell. In some embodiments, the down regulation of a *Jatropha* SDP1 gene provides enhanced seed oil accumulation in a transgenic or infected *Jatropha* plant, such as *Jatropha curcas*.

According to this aspect, the nucleic acid is selected to inhibit expression of the native gene or to silence the native gene within a plant's tissues to achieve a desired phenotype. In one embodiment, expression of the native gene is inhibited. Such inhibition might be accomplished, for example, with transformation of a plant cell to comprise a promoter linked to an antisense nucleotide sequence, hairpin, RNA interfering molecule, double stranded RNA, microRNA or other nucleic acid molecule, such that tissue-preferred expression of the molecule interferes with translation of the mRNA of the native DNA sequence or otherwise inhibits expression of the native DNA sequence in plant cells. For further description of RNAi techniques or microRNA techniques, see, e.g., U.S. Pat. Nos. 5,034,323; 6,326,527; 6,452,067; 6,573,099; 6,753,139; and 6,777,588. See also International Publication Nos. WO 97/01952, WO 98/36083, WO 98/53083, WO 99/32619 and WO 01/75164; and U.S. Patent Application Publication Nos. 2003/0175965, 2003/0175783, 2003/0180945, 2004/0214330, 2005/0244858, 2005/0277610, 2006/0130176, 2007/0265220, 2008/0313773, 2009/0094711, 2009/0215860, 2009/0308041, 2010/0058498 and 2011/0091975. RNAi molecules or microRNA molecules can be prepared by the skilled artisan using techniques well known in the art, including techniques for the selection and testing of RNAi molecules and microRNA molecules that are useful for down regulating a *Jatropha* SDP1 gene. In another embodiment, the native gene may be silenced by using VIGS. Such silencing may be accomplished by infecting a *Jatropha* plant with a VIGS system that contains at least a partial fragment of a candidate gene to be silenced. For further description of VIGS systems, see International Publication Nos. WO 2010/080071 and WO 2010/144058.

The construct typically includes regulatory regions operatively linked to the 5' side of the nucleic acid described herein (such as a nucleic acid encoding a *Jatropha* SDP1 protein or a nucleic acid encoding an RNAi molecule to down regulate a *Jatropha* SSDP1 gene) and/or to the 3' side of the nucleic acid. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. The promoters and tissue-specific promoters, such as seed promoters and especially *Jatropha* seed promoters, are particularly useful for preparing constructs for the transformation of *Jatropha*.

Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670, 2006/0248616 and 20090100536, and the references cited therein. The expression cassettes may additionally contain 5' leader sequences in the expression cassette construct. Such leader sequences can act to enhance translation. Translation leaders are known in the art and include those described in International Publication No. WO 2008/094127 and the references cited therein.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV 35S promoter (Odell et al., 1985); rice actin (McElroy et al., 1990); ubiquitin (Christensen and Quail, 1989; Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880. Any other recourse seed specific promoter can be used to, for example, *Jatropha* oleosin promoter (Popluechai et al., 2011), 2S storage protein promoter, the *Jatropha* SDP1 promoter described herein, and the like.

Generally, the expression cassette may additionally comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, International Publication No. WO 02/36782, U.S. Pat. No. 7,205,453 and U.S. Patent Application Publication Nos. 2006/0218670, 2006/0248616, 2007/0143880 and 2009/0100536, and the references cited therein. See also, Jefferson et al. (1991); De Wet et al. (1987); Goff et al. (1990); Kain et al. (1995) and Chiu et al. (1996). This list of selectable marker genes is not meant to be limiting. Any selectable marker gene can be used. The selectable marker gene is also under control of a promoter operable in the plant species to be transformed. Such promoters include those described in International Publication No. WO 2008/094127 and the references cited therein.

Alternatively, the expression cassette may additionally comprise a Cre-lox recombination marker free system, such as described by Zuo et al. (2001). Such a system is useful for producing selection marker free transgenic *Jatropha* plants.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Once a nucleic acid has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

DNA constructs containing the promoters of the present invention can be used to transform any plant and particularly cotton plants. The constructs may be introduced into the genome of the desired plant host by a variety of conventional techniques. Techniques for transforming a wide variety of higher plant species are well known and described in the technical and scientific literature. Transformation protocols may vary depending on the type of plant or plant cell, i.e., monocot or dicot, targeted for transformation, as is well known to the skilled artisan. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Publication Nos. WO 2005/103271 and WO 2008/094127 and references cited therein. Techniques which have been used to transform oil palm include biolistic-mediated transformation and *Agrobacterium*-mediated transformation. See, for example, Masli et al. (2009); Omidvar et al. (2008); Parveez et al. (2008); Abdullah et al. (2005); Parveez et al. (2000); Chowdhury, et al. (1997); U.S. Patent Application Publication No. 2009/0038032; and International Publication No. WO 2010/071608.

Transformed plant cells which are derived by any of the above transformation techniques can be cultured to regenerate a whole plant which possesses the transformed genotype and thus the desired phenotype, e.g., a transgenic plant. A "transgenic plant" is a plant into which foreign DNA has been introduced. A "transgenic plant" encompasses all descendants, hybrids, and crosses thereof, whether reproduced sexually or asexually, and which continue to harbor the foreign DNA. Regeneration techniques rely on manipulation of certain phytohormones in a tissue culture growth medium, typically relying on a biocide and/or herbicide marker which has been introduced together with the desired nucleotide sequences. See for example, International Publication Nos. WO 2008/094127 and WO 2010/071608 and references cited therein.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular *Jatropha* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants. The culitvated transgenic plants will express the DNA of interest in a tissue-preferred or tissue-specific manner as described herein.

In a fifth aspect, the present invention provides methods of increasing seed oil accumulation in *Jatropha*, such as *Jatropha curcas*. In one embodiment, a method involves modulating the level of activity of a Sugar-dependent 1 (SDP1) gene, such as JcSDP1 gene, which encodes a patatin-domain triacylglycerol lipase in the host *Jatropha* cell or *Jatropha* plant. The level of activity of the lipase can be reduced by reducing expression of the SDP1 gene. In one embodiment, the modulation of the level of activity of the lipase is a reduction in the activity of the lipase. The level of activity of the lipase can be reduced by using RNAi techniques described herein in which the lipase is the target for the RNAi. Alternatively, the level of activity of the lipase can be reduced using VIGS techniques as described herein in which at least a partial fragment of the target gene is used. In one embodiment, *Jatropha* RNAi plants accumulate about 13% to about 30% higher seed oil than control plants.

The present invention shows that SDP1-deficiency enhances seed oil accumulation in the model plant *Arabidopsis*. Based on this result, RNAi technology and the native JcSDP1 promoter was used to generate transgenic *Jatropha* plants with reduced endogenous SDP1 expression. The present invention shows that SDP1-deficient transgenic *Jatropha* plants, such as those produce by RNAi technology, accumulate about 13% to about 30% higher seed oil than control plants. Free fatty acid content in seed was reduced from about 27% in WT to about 8.5% in SDP1-deficient transgenic *Jatropha* plants, such as those produce by RNAi technology. This transgenic technology leads to an enhanced agronomic trait for this biodiesel crop.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized. The following abbreviations are used: DAP: Days After Pollination; FAME: Fatty Acid Methyl Ester; FFA: Free Fatty Acid; GC: Gas Chromatography; GC/MS: Gas Chromatography/Mass Spectrometry; GUS: beta-glucuronidase; PTLs: Patatin-like TAG Lipases; qRT-PCR: Quantitative real time PCR; RNAi: RNA interference; SEM: Scanning Electron Microscopy; SDP1: Sugar-dependent1; TAGs: Triacylglycerols; TEM: Transmission Electron Microscopy; TLC: Thin Layer Chromatography; WAF: Weeks After Fertilization.

Example 1

Materials and Methods

Plant Materials and Growth Condition:
Arabidopsis Col-0 (*Arabidopsis thaliana* ecotype Columbia-0) was grown on soil with sand. Homozygous sdp1-5 mutant (Salk_076697, *Arabidopsis* Biological Resource Center, Ohio State University, Columbus, USA) seeds were stratified at 4° C. for 3 days on soil and cultured in a growth chamber under 16 hr-light/8 hr-dark cycles, 23° C.±3° C. and white light (100-150 $\mu Em^{-2}s^{-1}$ photosynthetically active radiation). Rosette leaves were harvested from 3 or 4 week-old plants and other organs such as inflorescence stems, cauline leaves, flowers, siliques, and developing seeds were harvested from 6 week-old plants. Seeds from siliques of 3 to 5 DAP (DAP: day after pollination) were used as the early stage of seed maturation in *Arabidopsis*. Leaves and developing fruits (S1; 1WAF, S2; 2 to 3WAF, S3; 4 to 6WAF, and S4; 7 to 8WAF, WAF: weeks after fertilization) were collected from *Jatropha* plants grown in a greenhouse.

RNA Isolation and Quantitative Real-Time PCR:
Total mRNA was isolated from plant samples using TRIzol reagent (Invitrogen, St. Louis, Mo., USA) according to the manufacturer's instructions. cDNA was synthesized with 1 µg total mRNA using MMLV Superscript II (Promega, Madison, Wis., USA) after DNase I treatment (Roche Applied Science, Mannheim, Germany). Quantitative real-time PCR assay was performed with an ABI 7900 sequence Detection. System (Applied-Biosystems, Foster City, Calif., USA). Power SYBR Green PCR Master Mix (Applied-Biosystems) reagent protocol was used but reduced the volume to 10 µL per reaction. As controls, the species-specific tubulin and actin primer sets for *Jatropha curcas* and *Arabidopsis thaliana*, respectively, were used. Fold change values of the target gene transcripts were subsequently normalized by dividing the ΔCt values with the ΔCt values of each control gene transcript. All real time PCR experiments were performed in triplicates using different biological samples.

Isolation of JcSDP1 Full Length cDNA and its Promoter:
A partial SDP1 sequence in our *Jatropha curcas* EST database was found. Using this partial sequence, 5' or 3' cDNA RACE primers were designed and RACE experiments were performed using BD SMART™ RACE cDNA Amplification Kit (BD Bioscience Clontech, Franklin Lakes, N.J., USA). One µg total RNA derived from developing seeds (S2 to S3) was used for the generation of 5' or 3' RACE pools. The 5' and 3' cDNA ends were obtained by touchdown PCR with advantage 2 PCR Enzyme System (BD Bioscience Clontech) following the manufacturer's instructions. To specifically amplify the products, the primary RACE products were diluted and mixed with a nested gene specific primer (GSP2) and the nested universal primer mixture (AP2). The PCR products were gel purified, cloned into pDrive Cloning Vector (Qiagen, Düsseldorf, Germany) to obtain full-length JcSDP1 cDNA (2577-bp). The Universal GenomeWalker kit (BD Bioscience Clontech) was used to isolate the promoter fragment of the JcSDP1 gene. Genomic DNA was restricted by DraI, EcoRV, PvuII, SspI, and StuI endonuclease and five libraries of adaptor-ligated genomic fragments were constructed. These genomic DNA libraries were used as templates for the PCR reactions for promoter isolation. For each round of genome walking, the primary PCR products were amplified by a gene-specific primer (GSP1) and the outer adaptor primer (AP1). To the second PCR reaction mix, the primary products were diluted and used as templates with a nested gene specific primer (GSP2) and the nested adaptor primer (AP2). The secondary PCR products were then analyzed on agarose gels and the relevant DNA fragment purified with QIAEXII Gel Extraction Kit (Qiagen), cloned into pDrive Cloning Vector (Qiagen) and sequenced. Potential cis-elements in the promoter region were analyzed using computational analytical methods available on two public web-sites, PlantCare (http://bioinformatics.psb.ugent.be/webtools/plantcare) and PLACE (http://www.dna.affrc.go.jp).

Construction of Pro JcSDP1:GUS Fusion Gene and Promoter Analysis:
pKGWFS7 destination vector including GFP or GUS reporter gene was used for promoter analysis. The 5'-flanking region of JcSDP1 was amplified using two specific primers, JcSDP1-PF1T and JcSDP1-PR1. This promoter was 873-bp in length, including 149-bp of 5' untranslated region (UTR). The amplified PCR product was inserted into TOPO donor vector using the pENTR™/D TOPO Cloning Kit (Invitrogen), and then inserted into the destination vector, pKGWFS7, using the Gateway LR Clonase™ II enzyme mix (Invitrogen). For plant transformation, the constructs were introduced into *Agrobacterium tumefaciens* strain AGL1 using electroporation. Constructs were transformed into WT (Col-0) or sdp1-5 mutant (Salk_076697) background through the floral dip method described by Clough and Bent (38).

For transient assay of JcSDP1 promoter expression, 10 µg of ProJcSDP1:GUS in pKGWFS7 plasmid DNA was coated with 1 µm diameter gold particles (2.5 mg gold particles, 200 µL of 2.5 M $CaCl_2$ and 100 µL of 0.1 M Spermidine). After incubating on ice for 30 min, the pellet of DNA/gold particle was washed twice with 70% ethanol and re-suspended in 100% ethanol. *Jatropha* fruits and leaves were centered in a petri-dish containing MS agar medium (39). Fruits and leaves were bombarded at 1,350 psi with a biolistic helium gun device (Bio-rad PDS-1000/He, USA). After incubation for 2 days at 25° C. the bombarded tissues were analyzed by histochemical assays as described by Jafferson et al. (40). The tissues were incubated in GUS staining buffer [0.1 M Sodium phosphate (pH 7.0), 1 mM 5-bromo-4-chloro-3-indolyl-D-glucuronide (Sigma, St Louis, Mo., USA), 0.5 mM potassium ferrocyanide, 0.5 mM potassium ferricyanide, 10 mM $Na_2EDTA$, and 0.1% Triton X-100] for 20 hrs at 37° C. Stained tissues were rinsed with 70% to 80% ethanol until pigments such as chlorophylls had been cleared. Selected organs of ProJcSDP1:GUS transgenic *Arabidopsis* lines were analyzed for GUS expression. To investigate the sugar-responsive expression of JcSDP1 promoter, we used 14 days-old seedlings of T2 lines and incubated for 24 hrs in an MS media with 1% or 3% of a sugar source: sucrose, fructose, and glucose. Mannitol was used as a control for osmotic stress.

Complementation of the JcSDP1/Sdp1-5 Mutation in *Arabidopsis*:

Full-length JcSDP1 cDNA was cloned into a vector harboring a tandem CaMV35S promoter and a Nos polyA addition sequence from pCAMBIA 1300 and transformed into *Arabidopsis* sdp1-5 mutant (Salk_076697). T1 transformants were selected on 40 μg/mL hygromycin and T2 seedlings were assayed for sugar responses on MS agar plates without sucrose.

Construction of Inducible Marker-Free ProJcSDP1: JcSDP1-RNAi Vector and Transformation to *Jatropha* Plants:

The pCCreloxP (pCCLB3) inducible marker free vector system was used as described by Qiu et al. (41). The T-DNA of pCCreloxP vector harbors a loxP fragment that consists of CRE-int, HPT and XVE genes (FIG. 5A). To silence JcSDP1 expression using RNAi a 373-bp fragment was selected that includes 290-bp 3' coding region of JcSDP1 cDNA with a stop codon and 83-bp of the 3' UTR region. The 373-bp JcSDP1 fragment was amplified with two primer sets, JcSDP1-RNAiF-XhoI and JcSDP1-RNAiR2-HindIII or JcSDP1-RNAiF-BamHI and JcSDP1-RNAiR2-PstI, used for the sense orientation or antisense orientation, respectively, and the fragments were then cloned into pBluescript SK intron vector (pBS-Ski) which has an intron (156-bp) to generate pJcSDP1-RNAi as previously described (42). ProJcSDP1 was amplified with two primers, JcSDP1-PF1-ApaI and JcSDP1-PR1-XhoI and then restricted with ApaI/XhoI. To insert the ProJcSDP1 (JcSDP1 promoter) fragment into the pJcSDP1-RNAi construct, we used ApaI and XhoI restriction enzyme sites in the pJcSDP1-RNAi. A 226-bp fragment containing the CaMV35S polyA addition sequence (T35S) was amplified with T35S-F-XbaI and T35S-R-PmlI-SacII primers. The amplified T35S fragment was cleaved with XbaI/SacII restriction enzymes and then cloned into ProJcSDP1-RNAi. Finally, the ProJcSDP1:JcSDP1-RNAi: $T_{35S}$ fragment from the ProJcSDP1-RNAi construct was inserted into the pCCreloxP marker free vector at the ApaI and PmlI sites. All constructs were introduced into *Agrobacterium tumefaciens* strain AGL1 using electroporation and then transformed into *Jatropha* using cotyledon explants (43).

Fatty Acid Analysis in *Arabidopsis* and *Jatropha*:

We used gas chromatography (GC) to analyze fatty acid profiles of the sdp1-5 mutant. (44). 100 dried seeds of each line were weighed and samples were transmethylated at 85° C. for 2 hrs in a reaction buffer (1 mL of 3 M HCl-methanol (Sigma), 25 μL of BHT solution (Sigma), and 300 μL of toluene (Sigma)). 50 μg of pentadecanoic acid (C15:0, Sigma) was added to each sample as an internal standard. After being cooled down to room temperature, 1.5 mL of 0.9% NaCl (w/v) was added to the mix and the fatty acid methyl esters (FAMEs) were extracted two times with 1 mL of hexane. Extracts were evaporated under nitrogen and then dissolved in 100 μL of the hexane. The final extracts were analyzed with GC using a flame ionization detector (FID) on Agilent 6890 (Agilent, Santa Clara, Calif., USA) employing helium as the carrier gas. Total fatty acids were estimated by comparing the total FAME peak area (pA*sec) to that of the C15:0.

To analyze fatty acid content in *Jatropha* transgenic lines, dried endosperm of seed was used as described previously (7). *Jatropha* samples were transmethylated at 70° C. for 20 min in a reaction buffer (1 mL of 3 N methanolic-HCl, 400 μL of 2,2, dimethoxypropane (Sigma) and 50 μg of pentadecanoic acid (C15:0)). After being cooled down to room temperature, the fatty acid methyl esters (FAMEs) were washed with 1 mL of water and 1 mL hexane twice. The extracts were evaporated under nitrogen and then dissolved in 500 μL of hexane. The final samples were analyzed by GCMS-QP2010 (Shimadzu Corporation, Japan). Standard deviation was calculated based on several different plants.

Analysis of Lipids by TLC and Quantification by GC/MS:

Seed lipids were extracted with hexane three times (7, 44). After determination of total lipid amount, 300 μg of neutral lipid were fractionated by TLC (Thin Layer Chromatography) on silica gel plates in a running solvent mixture, hexane: ethyl acetic acid: acetic acid (90:10:1 by vol). Triolein (Sigma T7140) and Oleic acid (Sigma 75090) were used as a standard of TAG and of FFA, respectively. TLC plates were exposed to iodine ($I_2$) vapor for visualization. The separated neutral lipid species including TAG and FFA were recovered from the plates using hexane and quantified by GC/MS after conversion to their corresponding methyl esters by methanolic-HCl method according to Li et al. (44). The absolute amount was calculated against the C15:0 internal standard by comparing their relative peak areas.

TEM and SEM Analysis:

TEM was performed with mature dried seeds of WT (Col-0) and sdp1-5 mutant. Seeds were embedded in resin and sectioned by an ultramicrotome (Leica Ultracut UCT; Leica, Germany) set at 70-nm thickness. Sectioned samples were placed onto 300 mesh cooper grids. Sections were observed and pictures were taken with transmission electron microscope (JEM-1230; JEOL, Japan) at 120 kV. For SEM analysis dried seeds were mounted directly and observed using a JSM-6360LV (JEOL, Japan) with an acceleration voltage of 20 kV.

Seed Weight and Size Measurement:

Mature seeds were harvested from WT (Col-0) and sdp1-5 mutant grown under the same conditions. Sample size of 100 seeds per WT (Col-0) or sdp1-5 mutant was used to obtain an average seed weight with at least five times biological replications. Average values are given along with SD (n=5). The Leica DM5000B microscope (Germany) and Image) analysis software were used to measure seed sizes. Average values are given along with SD (n=10).

Primers:

Sequence information on primers used in the experiments is set forth in Table 1 The SEQ ID NO: is set forth in parenthesis.

TABLE 1

| Primer Sequences | | |
|---|---|---|
| Promoter analysis | | (SEQ ID NO:) |
| | JcSDP1-PF1T | CACCtacatccagtagattgcacgtcacacacta (8) |
| | JcSDP1-PR1 | ctctaaaagtttcgtgttttggatgatttgct (9) |

TABLE 1-continued

Primer Sequences

| Promoter analysis | | (SEQ ID NO:) |
|---|---|---|
| Gene construction | | |
| | JcSDP1-CF-Sal | ttggtcgacatggatataagtaatgaggccaatgt (10) |
| | JcSDP1-CR-Nhe | attgctagcaccatccacagaactttgatcctgtc (11) |
| | JcSDP1-RNAiF-Xho | atactcgagtccataatgggattgtgttgaacgtcgt (12) |
| | JcSDP1-RNAiR2-H3 | tcgaagcttgctagtggcacttgatattaaggtgat (13) |
| | JcSDP1-RNAiF-Bm | ataggatcctccataatgggattgtgttgaacgtcgt (14) |
| | JcSDP1-RNAiR2-Pst | tctttctgcagctagtggcacttgatattaaggt (15) |
| | JcSDP1-PF1-ApaI | tatggggccctacatccagtagattgcacgtcacaca (16) |
| | JcSDP1-PR1-Xho | atgctcgagctctaaaagtttcgtgttttggatgattt (17) |
| | T35S-F-Xba | acttctagacggccatgctagagtccgcaa (18) |
| | T35S-R-Pml-SacII | ttaccgcggcacgtgaggtcactggattttt (19) |
| MF genotyping | | |
| | HygF | aaaaagcctgaactcaccgcgacgtct (20) |
| | HygR | tacttctacacagccatcggtcca (21) |
| | MF-P1 | ctgaattgtcgaggtcgaagatc (22) |
| | JcSDP1-R16 | agcagccaaatgggtctgtcc (23) |
| | T35S-R | cttctcattatcggtggtgaacat (24) |
| qRT-PCR | | |
| At2g37620 | AtActin F | ctctgtctggattggagggtc (25) |
| | AtActin R | gcttgagaaatggtcggaaa (26) |
| At4g25140 | AtOleo1-F | tgccgctataaccgttttctcttgga (27) |
| | AtOleo1-R | atgttccccaccagtatgttgctgtcc (28) |
| At5g40420 | AtOleo2-F | atgcggttggctacgcaggacaa (29) |
| | AtOleo2-R | tcatgcagccgtcgtcctcccct (30) |
| At5g51210 | AtOle3-F | tggaatagccgccattaccgcctt (31) |
| | AtOle3-R | agaaacttgttggtgttggactccaatg (32) |
| At5g04040 | AtSDP1-QF | atgccatcgattgggaacca (33) |
| | AtSDP1-QR | caccggttcttgtaaaccggaat (34) |
| | JcTubulin F | gaggctggatctggcaaacacgtt (35) |
| | JcTubulin R | tgtgtaatgacctctagcaaaatta (36) |
| | JcSDP1-QF | cataatgggattgtgttgaacgtcgt (37) |
| | JcSDP1-QR | gtcatcatcgtcatccccagcata (38) |
| Fatty acid related genes in Arabidopsis | | |
| At3g12120 | AtFAD2-F | cctcagcctctctcttacttggctt (39) |
| | AtFAD2-R | ccaggagaagtaagggacgag (40) |
| At2g29980 | AtFAD3-F | ctacttgttggtccataatgttcgtca (41) |
| | AtFAD3-R | cgtagataactccattccttgcct (42) |
| At4g34520 | AtFAE1-F | gtcttaaccaactttttcaacctctgtt (43) |
| | AtFAE1-R | ccaaaccgaaaacagtgaaagcaaagt (44) |

TABLE 1-continued

Primer Sequences

| Promoter analysis | | (SEQ ID NO:) |
|---|---|---|
| At3g05020 | AtACP1-F | aatctatccttcaacctccgccgt (45) |
| | AtACP1-R | agagaatctgctccaaggtcagct (46) |
| At5g15530 | AtBCCP2-F | ggatctcctttccctccgatgttt (47) |
| | AtBCCP2-R | ataaattcagagagctcggcgggt (48) |
| At3g22960 | AtCh-PK-F | tggcatcactggtctcccgatgt (49) |
| | AtCh-PK-R | tcatacctcttgatttcagtaacgaga (50) |
| At5g52920 | AtCy-PK-F | agtcactatcgtccttccggcacaa (51) |
| | AtCy-PK-R | cgctctgtacgattgctatttcctct (52) |
| At5g49190 | AtSUS2-F | tcaagtcagttcactgcagatctaat (53) |
| | AtSUS2-R | caactcggtaaagaccaggcatagtgaa (54) |
| At5g46290 | AtKAS1-F | tcgcaaaacacacatcacacac (55) |
| | AtKAS1-R | gtgattgacgatttgatggtaag (56) |
| At1g62640 | AtKASIII-F | tggtcttcctgatctgcc (57) |
| | AtKASIII-R | ccgcttctcactgcctcat (58) |

Protein and Carbohydrate Analysis:

Protein content in *Jatropha* transgenic lines was analyzed according to Focks and Benning (45) with 50 mg of dried endosperm. Protein amounts were measured by the Lowry DC protein assay (Bio-Rad) using gamma-globulin as a standard. To analyze carbohydrate content, 50 mg of dried endosperm were homogenized in 200 μL of assay buffer and centrifuged at full speed. The extracted supernatant was used for carbohydrate quantification using Total Carbohydrate Assay Kit (Sigma). D-glucose was used as a standard for calibration.

gDNA Isolation and Southern Blot:

Total genomic DNA was isolated from leaves from transgenic or control (CK; 35S:GFP) plants grown in a greenhouse. We used CTAB (cetyltrimethylammonium bromide, Sigma) method (46). Genomic DNA was digested with restriction enzymes and separated on 0.8% agarose gels. The gels were processed and blotted onto Hybond-N$^+$ membranes (Roche, Germany) following standard procedures (47). Probes were prepared with PCR DIG Labelling Mix using specific primer sets for Hygromycin phosphotransferase (HPT) gene and JcSDP1 gene. Hybridization was performed using the PCR DIG detection kit following the supplier's instructions (Roche, Germany).

Example 2

Sdp1-5 Accumulates TAG in Mature Dried Seeds

Figure 6:
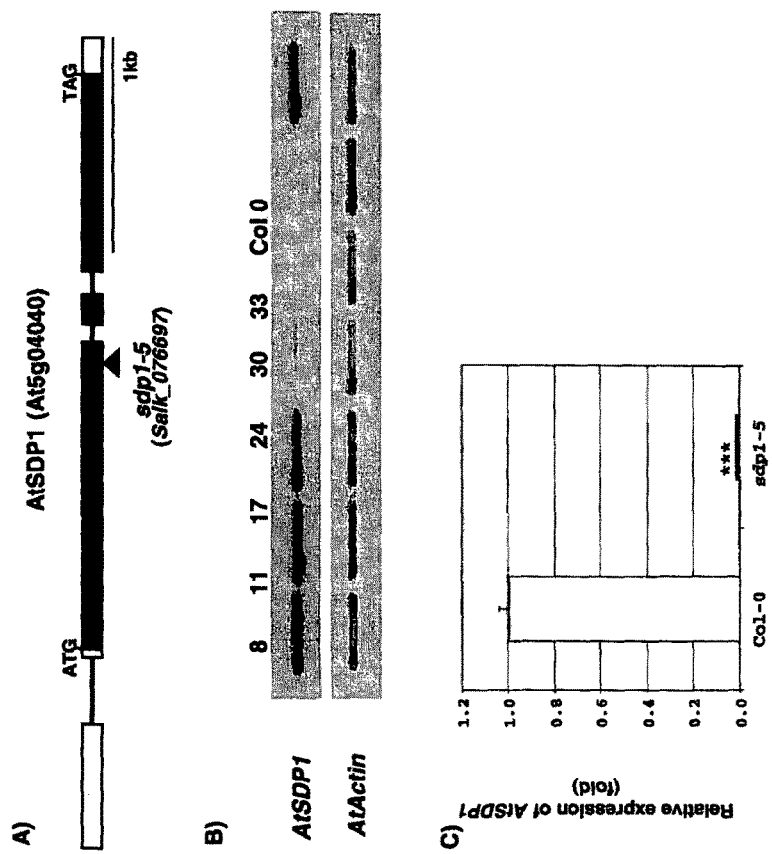
FIGS. 6A-6C show schematic diagram of SDP1 gene structure and insertion position of T-DNA in the sdp1-5 allele.

We obtained from the ABRC stock center an *Arabidopsis* mutant (Salk_076697) with T-DNA insertion in the SDP1 (At5g04040) locus and this mutant was designated sdp1-5 [15]. Using RT-PCR as a screen we obtained 3 homozygous lines (#24, 30 and 33) of the sdp1-5 null allele and one line (#33) was chosen for further experiments (Figure S1B). SDP1 transcript levels in sdp1-5 (#33) were 20-fold lower than in WT (Col-0) during early stages of seed development (3 to 5 DAP, DAP: Day after pollination) (FIG. 6C).

We first examined the effect of SDP1 deficiency on seed development, total fatty acid content and fatty acid profile. Scanning Electron Microscopy (SEM) analysis showed that sdp1-5 seeds were slightly larger than those of WT (Col-0) in length and width (FIG. 1A; Table 2). In addition, sdp1-5 seeds displayed an increase in dry weight of around 11.5% as compared to WT. To investigate the role of SDP1 in seed oil accumulation, total oil content and fatty acid composition in dried seeds were compared between WT (Col-0) and the sdp1-5 mutant. FIGS. 1 B and C show that the average dry seed weight of WT (Col-0) was about 19 μg containing approximately 5.54 μg of total fatty acids. The seed lipid content obtained by us is very similar to those reported by others, which is around 30-35% of dry seed weight. On the other hand, sdp1-5 seeds had an average dry weight of around 22 μg per seed containing 7.17 μg of total fatty acids. Therefore, sdp1-5 seeds have about 10% higher levels of total fatty acids compared to WT (Col-0) seeds (FIG. 1D). In addition, there was a clear increase in the relative proportion of unsaturated fatty acids, such as linolenic acid (C18:3) and eicosenoic acid (C20:1) in sdp1-5 seeds (FIGS. 1E and 1F). To characterize TAG accumulation in mature dried seeds, we analyzed total neutral lipid from WT (Col-0) and 3 homozygous lines of the sdp1-5 null allele by thin layer chromatography on silica gel plates. FIG. 1G shows reduced levels of free fatty acids (FFA) in sdp1-5 compared to WT (Col-0). Triolein and oleic acid were used as standards of TAG and FFA, respectively. To obtain quantitative data, we analyzed the samples using GC/MS and pentadecanoic acid (C15:0) was used as an internal control for quantitation. The sdp1-5 mutant had about 4.25% FFA and 95.75% TAG compared to 13.35% FFA and 86.65% TAG in WT (Col-0) (FIG. 1H).

TABLE 2

Seed Weight and Size of WT (Col-0) and sdp1-5

| Name | Weight of seed (µg/seed)[a] | Length of seed (µm/seed)[b] | Width of seed (µm/seed)[b] |
|---|---|---|---|
| Col-0 | 19.00 ± 1.10 | 481.12 ± 3.36 | 276.70 ± 10.58 |
| sdp1-5 | 21.00 ± 0.57**[c] | 522.86 ± 7.56*** | 294.29 ± 15.12* |

[a]Seed weight determination using 100 mature seeds. Average values are given along with SD (n = 5).
[b]The length and width of seed were measured using mature dried seeds. Average values are given along with SD (n = 10).
[c]*P < 0.05, P < 0.01 or *P < 0.001 versus WT (Col-0) seed.

Figure 7:
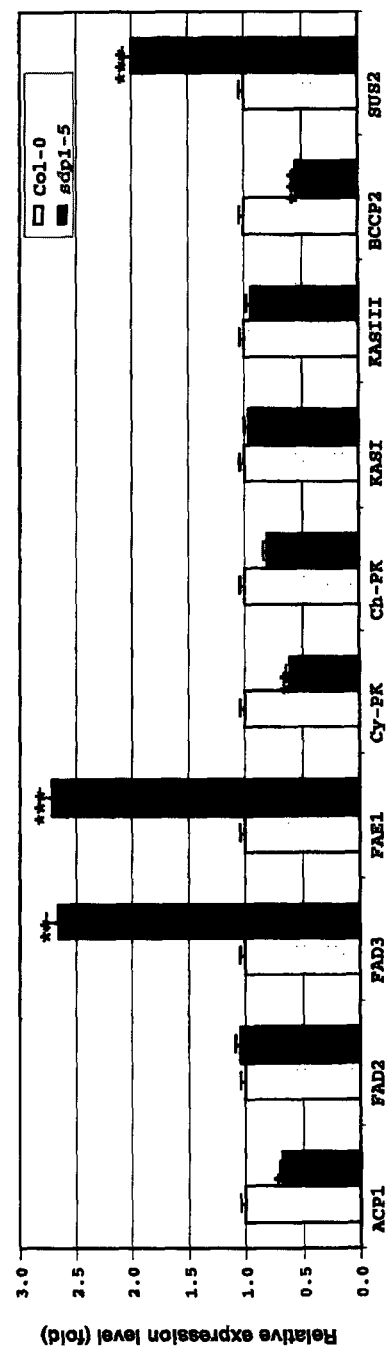
FIG. 7 shows expression profiles of fatty acid synthesis-related genes in early developing seeds of WT (Col-0) and sdp1-5. The cDNA library was synthesized from total mRNA derived from seeds (3 to 5 DAP). DAP: Days after pollination. Mean values are given with SD (n=3). ACP1 (acyl carrier protein; At3g05020), FAD2(oleate desaturase; At3g12120), FAD3(linoleate desaturase; At2g29980), FAE1 (fatty acid elongase; At4g34520), Cy-PK(cytosol pyruvate kinase; At5g52920), Ch-PK(chloroplast pyruvate kinase: At3g22960), KASI(ketoacyl-ACP Synthase I; At5g46290), KASIII(ketoacyl-ACP synthase III; At1g62640), BCCP2 (biotin carboxyl carrier protein; At5g15530), and SUS2 (sucrose synthase 2; At5g49190).

To examine the molecular basis of these changes in lipid content and fatty acid profile, we analyzed transcript levels of key genes involved in fatty acid biosynthesis. We found FAD3 was up-regulated in sdp1-5 (FIG. 7). Previously, Puttick et al. (17) reported that in Arabidopsis over-expression of FAD3 leads to an accumulation of high levels of linolenic acid and that is inversely correlated with linoleic acid (18:2) levels. We also observed an inverse correlation between linolenic acid and linoleic acids levels in sdp1-5 seeds. In addition, we found an increased accumulation of eicosenoic acid, a very-long-chain fatty acid that has been used as a metabolic marker for storage TAGs formation in Arabidopsis seeds (18). We found sdp1-5 seeds accumulated 1.3 µg of eicosenoic acid per seed which was 40% higher than that of WT (Col-0) seeds. The increased eicosenoic acid level in sdp1-5 seeds was likely due to the up-regulated Fatty Acids Elongase 1 (FAE1) (FIG. 7). Our results suggest that SDP1-deficiency is closely correlated with seed size augmentation, the relative proportion of unsaturated fatty acids and the accumulation of TAGs in mature seeds.

Example 3

Sdp1-5 Mutant has Increased Numbers of Oil Bodies in Dried Seeds

Figure 2:
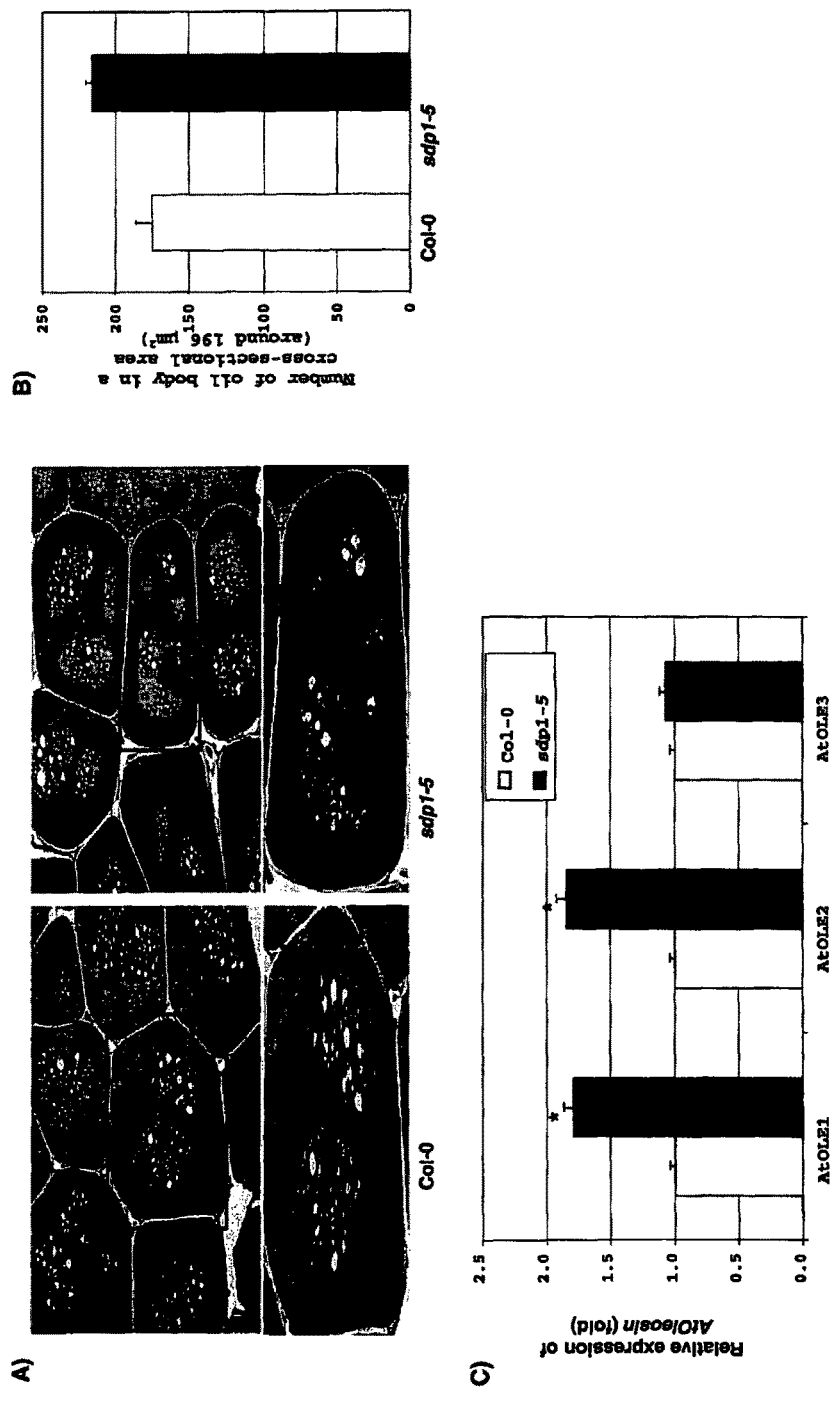
FIGS. 2A-2C show sdp1-5 mutant seeds produce more oil bodies.

Plant storage lipids, predominantly triacyglycerols (TAGs), are sequestered by monolayer phospholipids with embedded small proteins, such as oleosin, to form oil bodies (19). Previous work has highlighted the importance of oleosins for oil body structure and TAG accumulation in mature seeds. We used Transmission Electron Microscopy (TEM) to analyze the formation of oil bodies in sdp1-5 seeds. Mutant sdp1-5 seeds contained increased number of oil bodies but they were relatively smaller in size compared to those in WT (Col-0) seeds (FIG. 2A). The cross-sectional area of one mature seed cell was about 196 µm². Within this area, there were around 175 oil bodies in WT (Col-0) but about 216 oil bodies in sdp1-5, representing an increase of approximately 23% (FIG. 2B). Because oleosins are important proteins for seed oil body formation we investigated expression levels of 3 different oleosin genes in sdp1-5 by qRT-PCR. FIG. 2C shows transcript levels of AtOLE1 (At4g25140) and AtOLE2 (At5g40420) were two fold higher in sdp1-5 compared to WT (Col-0). These results suggest the increased number of oil bodies in sdp1-5 is possibly due to the enhanced expression of oleosins.

Example 4

JcSDP1 an Ortholog of AtSDP1 Rescues the SDP1-Deficiency in Arabidopsis

To investigate the impact of SDP1 deficiency in an oil seed crop, we isolated full-length JcSDP1 cDNA from Jatropha seed RNA samples using 5' and 3' cRACE technology. JcSDP1 encodes a protein of 858 amino acids with a molecular mass of approximately 96 kDa. A BLAST search revealed that JcSDP1 has high sequence homology (76%) to the Arabidopsis SDP1 (At5g04040). JcSDP1 has at least three predicted trans-membrane domains and four Site-1 protease (SIP) target sequences at the N terminus (RXXL; SEQ ID NO:5). Moreover, JcSDP1 has a conserved patatin domain with lipase activity sequences such as the oxyanion hole motif (GXGXXG; SEQ ID NO:6) and a lipase consensus motif with a catalytic serine (GXSXG; SEQ ID NO:7) (FIG. 3A). The high similarity of sequences and domains between JcSDP1 and AtSDP1 implied a possible similar function of JcSDP1 in TAGs metabolism. To investigate the function of JcSDP1 in TAG degradation during early stages of seed germination, we transformed JcSDP1 under the control of a CaMV35S promoter into the Arabidopsis sdp1-5 mutant. The Arabidopsis sdp1-5 showed retarded growth on sugar depleted MS medium and but the retarded growth can be rescued by the supplementation of 1% sucrose (15). Seven day-old seedlings of sdp1-5 plants expressing the heterologous JcSDP1 displayed normal growth on MS medium without sucrose whereas sdp1-5 mutant displayed retarded growth (FIG. 3B). This result indicates that JcSDP1 is able to rescue the retarded growth phenotype of sdp1-5 providing evidence JcSDP1 is an ortholog of AtSDP1.

Example 5

Characterization of JcSDP1 Promoter

Figure 4:
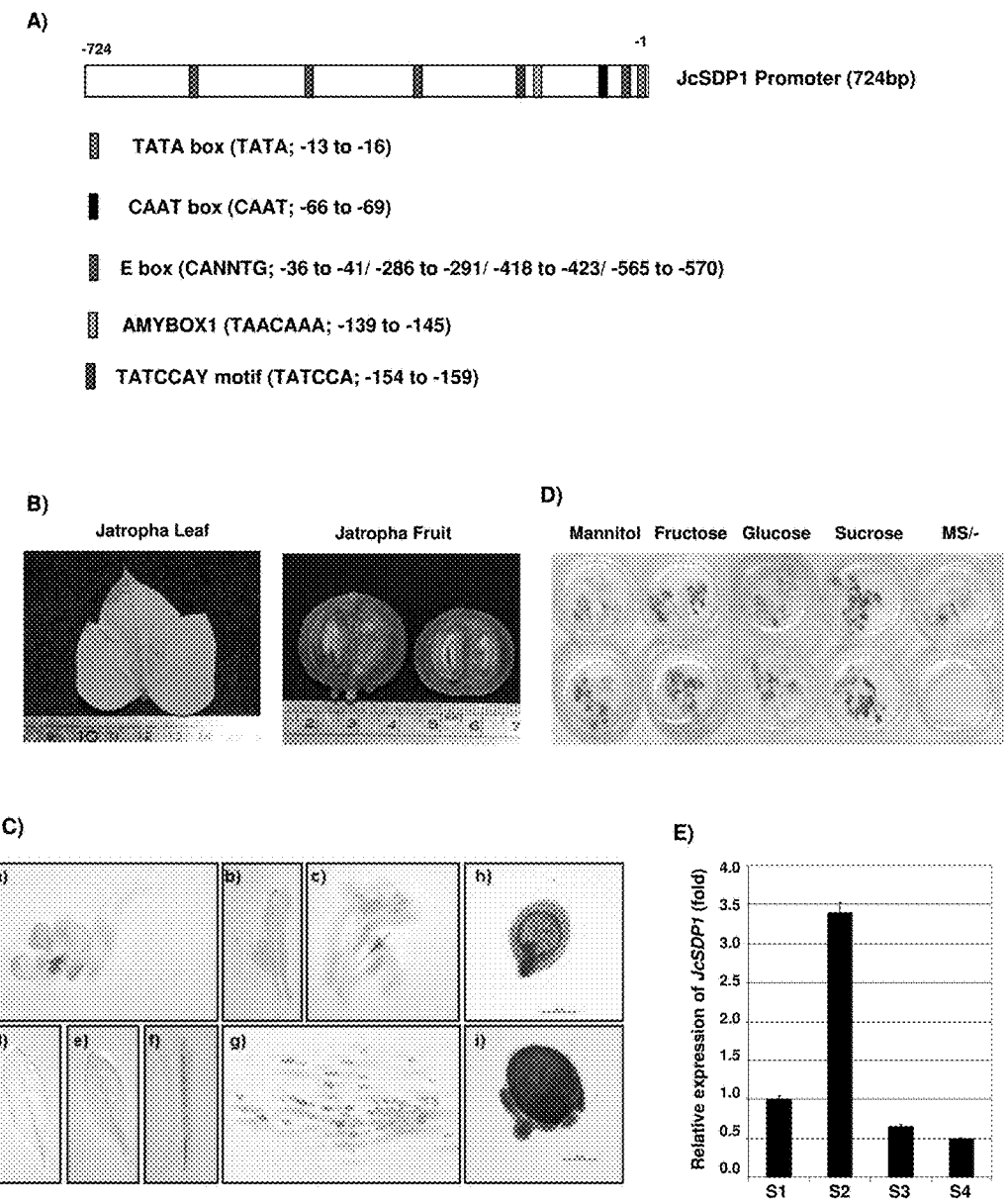
FIGS. 4A-4E show JcSDP1 promoter and its expression analysis in ProJcSDP1:GUS transgenic plants.

To specifically silence JcSDP1 gene expression in Jatropha, we isolated a native JcSDP1 promoter fragment from Jatropha genomic DNAs using a Genome Walker kit (Clontech). We cloned an approximately 0.7 kb fragment of JcSDP1 proximal to the 5'-UTR, which contained several putative cis-elements for gene expression and regulation. This region of the JcSDP1 promoter contains a TATA box and a CAAT box, located at −13 to −16 and −66 to −69, respectively. The promoter region also contains two putative sugar-responsive elements found in the alpha amylase gene, TATCCA and TAACAAA (20,21), located at −154 to −159 and −139 to −145, respectively. In addition the promoter fragment includes four E-box motifs, CANNTG (22, 23), which are likely involved in seed specific expression (FIG. 4A).

To see if the JcSDP1 promoter would show seed specific expressions, we generated a ProJcSDP1:GUS expression clone using the pKGWFS7 gateway vector system. The expression patterns of JcSDP1 promoter were examined in homologous and heterologous systems. To transiently analyze JcSDP1 expression in a homologous system, we introduced the ProJcSDP1:GUS fusion gene into developing fruits and leaf of Jatropha. We found the GUS gene was transiently expressed in developing Jatropha fruits, especially the endosperm part of the seed whereas leaf tissues did not show any GUS expression (FIG. 4B). This result suggests that the JcSDP1 promoter has seed-specific expression in Jatropha plant. We also analyzed JcSDP1-GUS expression in developing seeds of transgenic Arabidopsis plants expressing ProJcSDP1:GUS transgene. FIG. 4C shows that GUS expression was highly elevated at 3-4 days (globular embryos) after pollination (DAP) and also at 9-10 DAP (mature green embryos) (FIG. 4C-h and i) following the developmental stages described by Le et al. (24). These expression patterns were consistent with the expression pattern of JcSDP1 which was highly activated at stage S2 (3 WAF) (FIG. 4E). These results imply that the JcSDP1 promoter is controlled in a seed-specific and development dependent manner.

Using a cis-element prediction program we found that the JcSDP1 promoter carries two sugar-responsive alpha amylase elements, such as TATCCA and TAACAAA (20, 21). To investigate sugar responses of JcSDP1, we used 14 day-old transgenic *Arabidopsis* seedlings harboring the ProJcSDP1: GUS transgene. We examined the effects on GUS expression of sucrose, glucose, or fructose (1% or 3% concentration) supplementation in MS(-) media. As a control, mannose was used as a source of osmotic stress. FIG. 4D shows that the JcSDP1 promoter showed sugar-dependent expression, and the expression was especially responsive to sucrose and fructose.

Example 6

Figure 9:
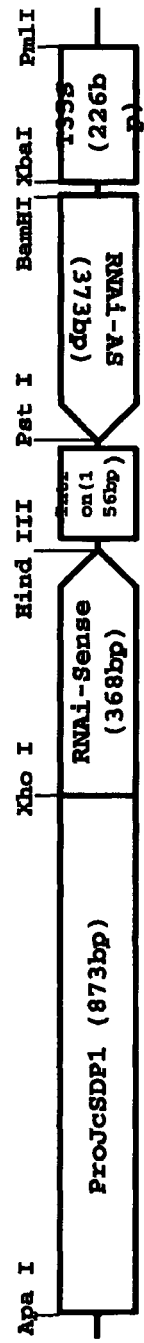
FIG. 9 shows a schematic diagram of a JcSDP1-RNAi sequence in accordance with one embodiment of the invention. A sequence for this construction is shown in SEQ ID NO:3

JcSDP1-RNAi Transgenic *Jatropha* Plants Accumulate Increased Storage Lipids in Their Endosperm We were interested to see if the reduction of SDP1 expression in *Jatropha* plants would also lead to an increased seed oil accumulation. To this end, we generated JcSDP1-RNAi transgenic *Jatropha* plants. To specifically control lipid accumulation in the mature seeds without ectopic gene silencing, we placed the JcSDP1-RNAi transgene under the control of a native JcSDP1 promoter (FIG. 9; SEQ ID NO:3) which is specifically expressed in *Jatropha* seeds. Through a two step selection process using hygromycin and β-estradiol, marker free or non-marker free transgenic plants were screened. These plants were further confirmed by genotyping with specific primer sets for HygF and HygR for the hygromycin gene and P1 and R16 or P1 and T35S-R for the marker free transgene. Based on the genotyping results, we obtained chimeric (heterozygote) marker-free plants in which the antibiotic selection marker was partially removed by homologous recombination. The transgenic lines displayed normal growth patterns and growth rates, leaf number and leaf size (FIG. 5B, panels d and e). In contrast to the enlarged seed size found in *Arabidopsis* sdp1-5, T1 mature seeds from JcSDP1-RNAi plants were normal in size (FIG. 5B, panels a, b, and c). To investigate oil content in T1 mature seeds, we carefully separated endosperms from embryos. Whereas the endosperms were used for further molecular and biochemical analysis, the embryos were regenerated to maintain the transgenic lines. After transgenic plants were fully grown and mature, we harvested mature seeds from four individual transgenic plants for further studies. Compared to control (CK) plants (35S:GFP lines), all tested transgenic lines accumulated increased oil content per dry seed weight in their endosperm (FIG. 5C). Endosperm of the best transgenic line (#158) accumulated raw oil content to about 54% of the dry seed weight; this represented a 30% increase of total oil in transgenic plants compared to 35S:GFP control (CK) plants. We analyzed JcSDP1-RNAi transgenic line #158 to investigate possible changes in protein and carbohydrate content along with the increased in lipid accumulation in endosperm. The protein content per endosperm of JcSDP1-RNAi decreased about 7% compared to the CK (35S:GFP) plant as shown in Table 3. However, no difference in the carbohydrate content was detected between the two.

TABLE 3

Protein and Carbohydrate Contents in Endosperm of Control (CK; 35S:GFP) and JcSDP1-RNAi Transgenic Plants

| Genotype | Total Lipid Content (%, w/w) | Protein Content (%, w/w) | Carbohydrate Content (%, w/w) |
| --- | --- | --- | --- |
| CK (35S:GFP) | 41.41 ± 2.19 | 14.93 ± 0.16 | 13.89 ± 0.12 |
| JcSDP1-RNAi #158 | 54.17 ± 2.13 | 13.99 ± 0.19 | 13.92 ± 0.13 |

Values are the mean ± SE of measurements on endosperms from individual seed (n = 4) of JcSDP1-RNAi #158 T1 transgenic and control (CK; 35S:GFP) plants grown in a greenhouse.

Figure 8:
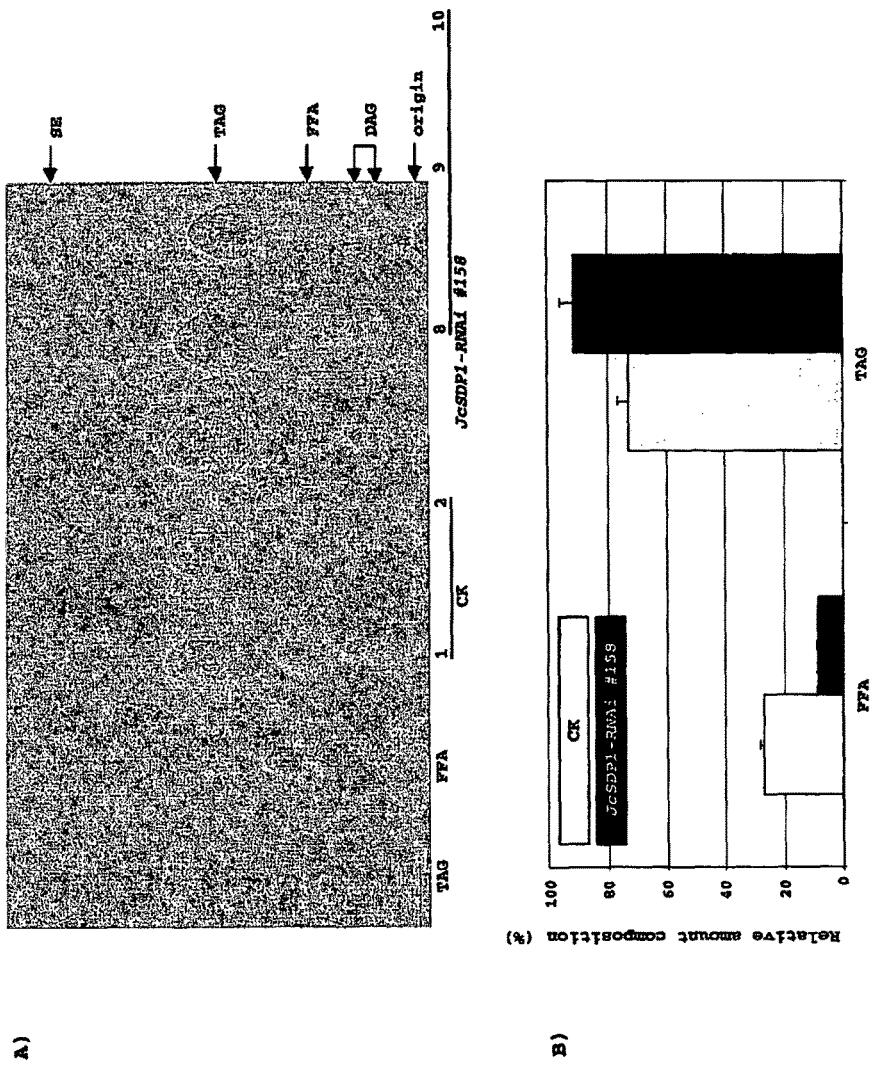
FIGS. 8A and 8B shows analysis of lipid composition of mature dried endosperm of JcSDP1-RNAi by TLC and GC/MS.
Figure 10:
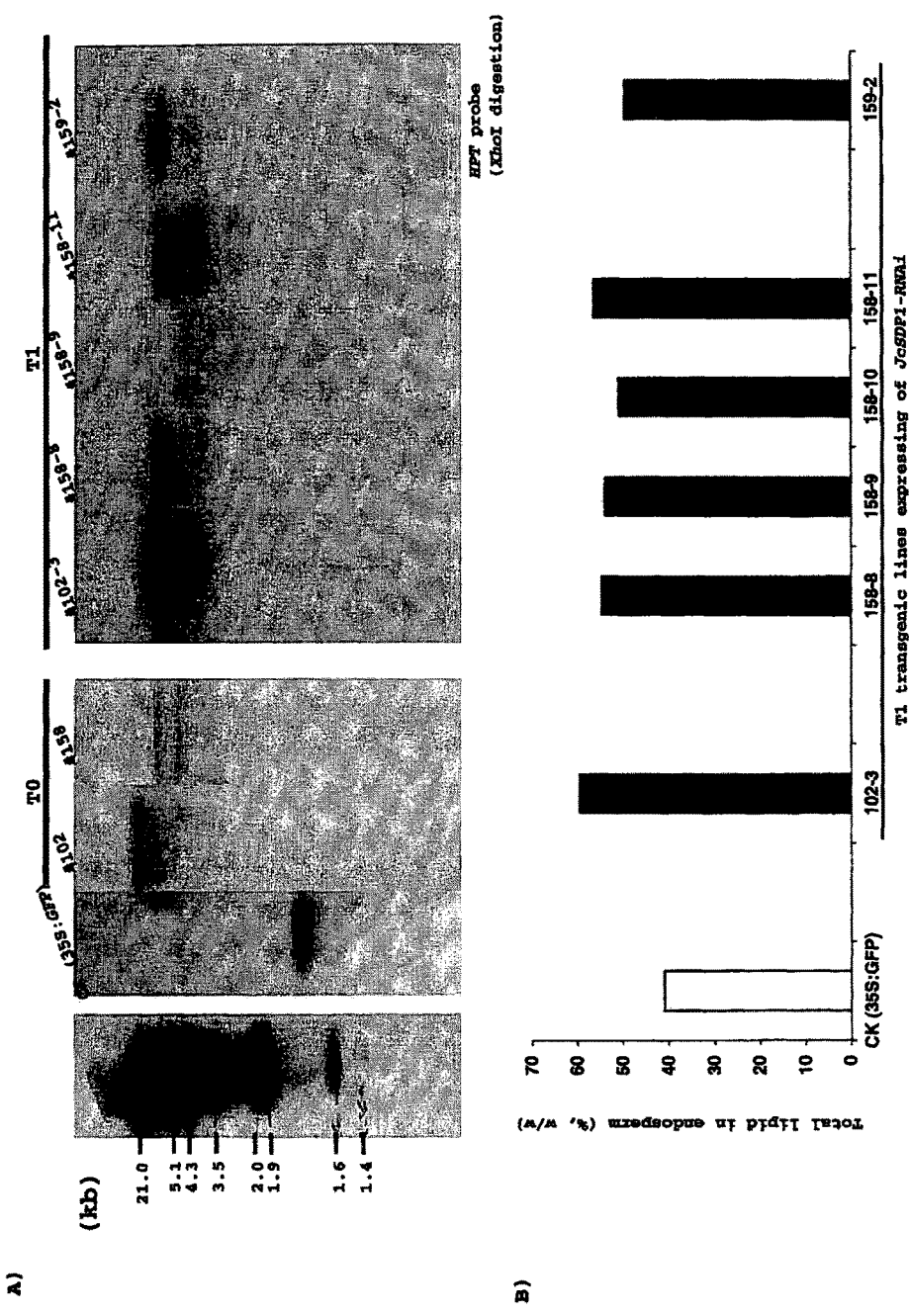
FIGS. 10A and 10B show Southern blot analysis of T0 and T1 transgenic plants expressing JcSDP1-RNAi.

To characterize TAG accumulation in mature endosperm, we analyzed total neutral lipid from CK and 3 individual lines of #158 transgenic plants by thin layer chromatography on silica gel plates. FIG. S3A shows reduced levels of free fatty acids (FFA) in the #158 transgenic line compared to CK. In addition, the #158 transgenic plants had about 8.49% FFA and 91.50% TAG compared to 26.83% FFA and 73.17% TAG in CK plants (FIG. 8B). We verified the number of T-DNA insertions in the best transgenic lines by Southern blot analysis (See Additional file 4). Among the T1 progeny plants of the parental line #158, we recovered a line (#158-8) that carried a single T-DNA insert and another line (#158-11) with multiple inserts. Regardless of the copy number of insertion, both #158-8 and #158-11 showed a very similar level of total seed lipid accumulation (FIGS. 10A and 10B).

To determine possible alterations in fatty acid profiles of JcSDP1-RNAi transgenic lines, we analyzed extracts by gas chromatography-mass spectrometry (GCMS-QP2010). FIG. 5D shows that JcSDP1-RNAi transgenic plants displayed a very similar fatty acid profile to that of CK plants. In contrast to the changes of fatty acids in the *Arabidopsis* mutant sdp1-5, we were unable to find any significant accumulation of C20:1 (less than 0.5% of total TAGs) in the transgenic *Jatropha* lines. The observed differences between the effects of SDP1 knock-down in *Arabidopsis* and *Jatropha* might be caused by physiological differences in oil accumulation. Indeed, reductions of JcSDP1 transcript levels were observed in JcSDP1-RNAi transgenic lines (FIG. 5E). Moreover, the increased oil accumulation in seeds was inversely correlated to the residual JcSDP1 transcript levels as assayed by quantitative real-time PCR (qRT-PCR). Taken together, we conclude that that suppression of JcSDP1 expression using RNAi technology can lead to enhanced oil accumulation in mature dried *Jatropha* seeds.

Example 7

SDP1-Deficiency Enhances Total Seed Oil Accumulation in *Arabidopsis* and *Jatropha*

The breakdown of TAGs into fatty acids is initiated by lipases many of which have been identified in eukaryotes including plants, yeast and animals (11, 12, 25). One of the characterized lipases is encoded by the *Arabidopsis* SUGAR DEPENDENT1 (SDP1). This lipase contains a patatin-like domain and is tightly associated with the oil body (13, 26, 27). Three SDP1 homologous genes have been identified in *Arabidopsis* and all 3 play important roles in storage oil mobilization (13, 14, 28). Besides its role in seed germination SDP1 is also active during the seed desication stage to hydrolyze TAGs (15).

Seed development in *Arabidopsis* consists of two major phases: early embryogenesis which is completed within 6 days after pollination (DAP) and seed maturation phase. The latter process can be further defined into three sub stages; early-maturation, mid-maturation and late-maturation. In the early-maturation stage embryos accumulate increasing amount of starch and begin to synthesize storage oils and proteins (7-10 DAP). During the mid-maturation stage (11-16 DAP) the amount of starch is dramatically reduced and this is inversely related to the accumulation of oils and proteins. Finally, in the late-maturation stage which is also known as desiccation stage, embryos gradually become metabolically quiescent with the exception that they synthesize sugars such as sucrose and trehalose to maintain integrity during the desiccation processes (29, 30). Chia et al. (14) reported that TAGs in oil bodies are important carbon sources for the proceeding of desiccation in late-maturation stage. During the desiccation process, around 10-14% of TAGs are consumed as carbon sources. Many enzymes, such as malate synthase (MS), isocitrate lyase (ICL), 3-ketoacyl CoA thiolase (KAT), hydroxyacyl CoA dehydrogenase (HD), enoyl hydratase (EH), and phosphoenolpyruvate carboxykinase (PEPCK), are involved to metabolize TAG (11, 12, 25). The Arabidopsis sdp1/sdp1L double knockout mutant display a similar phenotype as the glyoxylate cycle mutant id or 02, which lacks isocitrate lyase. These mutants are unable to synthesize carbohydrates from fatty acids (28, 31). In the sdp1-5, TAG degradation is almost completely blocked because SDP1 is the first enzyme for TAG metabolism in the desiccation process of the late-maturation stage (15, 28).

Based on these studies, we hypothesized that SDP1-deficiency might block TAG metabolism during the desiccation process thereby reducing the loss of TAG in the late-maturation stage. To test this hypothesis we isolated the Jatropha SDP1 homolog and showed that it is functional equivalent to the Arabidopsis SDP1 by genetic complementation of the Arabidopsis sdp1-5 mutant (FIG. 3B). Moreover, we showed SDP1-deficiency generated by RNAi technology produced a notable increase of seed oil accumulation in transgenic Jatropha plants. Our results suggest that the technology can be applied to enhance seed oil accumulation in other oil seed crops as well. It is possible that seeds of SDP1-deficient transgenic plants may be partially blocked in the desiccation process which may negatively impact their long-term shelf life. Moreover, the inhibition of TAG degradation may retard seedling growth and reduce seedling vigor. However, in the case of Jatropha, these issues can be mitigated by the industrial scale production of clonal transgenic plants by tissue culture. In addition, the issue of reduced seedling vigor can be obviated by germinating seeds in a sucrose-supplemented medium and selling germinated seedlings.

In this work, we have used the seed-specific promoter of JcSDP1 for regulated expression of the JcSDP1-related RNAi construct. The JcSDP1 promoter was chosen because we showed its activity peaks in the early stage of developing seed and gradually returns to basal levels in the late stage (FIG. 4E). Moreover, the JcSDP1 promoter is responsive to sugars, especially sucrose and fructose (FIG. 5). Based on these findings, we used the JcSDP1 promoter to express JcSDP1-related RNAi sequence so as to establish a feed-back inhibition system. For instance, if the gene silencing is not strong enough to knock down JcSDP1 expression, the residual JcSDP1 would degrade TAGs into free fatty acids which can be converted into sucrose, trehalose, and proteins. Once sucrose is elevated to a certain critical level in the endosperm, it can activate the JcSDP1 promoter which then in turn enhances the suppression of JcSDP1 gene expression. The gene silencing strategy we showed here has several advantages over the use of a CaMV35S promoter: 1) using the cognate promoter of a target gene can offer more specific regulation of the RNAi-dependent gene silencing against the target gene itself; 2) the end product of the target gene can be used for its own feed-back suppression; and 3) reduced ectopic expression of transgene.

Example 8

SDP1-Deficient Transgenic Jatropha Plants are Advantageous for the Process of Biodiesel Production Biodiesel is commonly produced from crude oil by alkaline or acid-treatment processes which are known as trans-esterification (32, 33). Owing to the short reaction time and reduced energy consumption, the alkaline-treatment process is the preferred method for trans-esterification. For the alkaline-treatment process, crude oil should contain a very low levels of free fatty acids (FFAs) and moisture because a high level of FFA and water can transform trans-esterification into saponification leading to easy depletion of catalysts (34, 35). For crude oil containing a high amount of FFAs and water acid treatment is more suitable; however, the reaction time of acid treatment is very long and there is a greater requirement of alcohol. This dilemma has prompted studies to improve trans-esterification processes by chemical methods (36, 37). The deficiency of seed-specific SDP1 in Jatropha plant provides a solution to the dilemma. FFA levels of mature seeds are mainly determined by SDP1 during the desiccation step at the late-maturation stage (15, 28). Here, we showed that in mature dry seeds JcSDP1-RNAi transgenic lines contain higher TAG levels and lower FFA levels compared to control Jatropha plants (FIG. 1C-1D and FIG. 5C). Therefore, crude oils derived from SDP1-deficient transgenic Jatropha plants are a better substrate compared to WT crude oil for alkaline trans-esterification in biodiesel production.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. IEA says "Biofuels can displace 27% of transportation fuels by 2050 Washington". *Platts.* 20 Apr. 2011.
2. Gubitz G M, Mittelbach M, Trabi M: Exploitation of the tropical oil seed plant *Jatropha curcas* L. *Bioresource Technol* 1999, 67:73-82.
3. Carels N: *Jatropha curcas*: A review. *Advances in Botanical Research* 2009, 50:39-86.
4. Adebowale K O, Adedire C O: Chemical composition and insecticidal properties of the underutilized *Jatropha curcas* seed oil. *African Biotechnol* 2006, 5:901-906.
5. Openshaw K: A review of *Jatropha curcas*: an oil plant of unfulfilled promise. *Biomass Bioenergy* 2000, 19:1-15.
6. Kumar S, Sharma S: An evaluation of multipurpose oil seed crop for industrial uses (*Jatropha curcas* L.). *A Review Ind Crops Prod* 2008, 28:1-10.
7. Qu J, Mao H-Z, Chen W, Gao S-Q Bai Y-N, Sun Y-W, Geng Y-F, Ye J: Development of marker-free transgenic *Jatropha* plants with increased levels of seed oleic acid. *Biotechnol Biofuels* 2012, 5:10-20.
8. Stymne S, Stobart A K: Triacylglycerol biosynthesis. In The Biochemistry of Plants, Lipids: Structure and Function. Volume 9, Stumpf P K editor (New York: Academic Press) 1987, 175-214.
9. Murphy DJ: Plant Lipids: Biology, Utilization and Manipulation. Oxford, UK: Blackwell Publishing 2005.
10. Dutta S, Ray L: Production and characterization of an alkaline thermostable crude lipase from an isolated strain of *Bacillus cereus* C7. *Appl Biochem Biotechnol* 2009, 159:142-154.
11. Athenstaedt K, Daum G: YMR313c/TGL3 encodes a novel triacylglycerol lipase located in lipid particles of *Saccharomyces cerevisiae*. *J Biol Chem* 2003, 278:23317-23323.
12. Gronke S, Mildner A, Fellert S, Tennagels N, Petry S, Muller G, Jackie H, Kuhnlein R P: Brummer lipase is an evolutionary conserved fat storage regulator in *Drosophila*. *Cell Metab* 2005, 1:323-330.
13. Eastmond P J, Rawsthorne S: Coordinate changes in carbon partitioning and plastidial metabolism during the development of oilseed rape embryos. *Plant Physiol* 2000, 122:767-774.
14. Chia T Y P, Pike M J, Rawsthorne S: Storage oil breakdown during embryo development of *Brassica napus* (L.). *J Exp Botany* 2005, 56:1285-1296.
15. Eastmond P J: SUGAR-DEPENDENT1 encodes a patatin domain triacylglycerol lipase that initiates storage oil breakdown in germinating *Arabidopsis* seeds. *Plant Cell* 2006, 18:665-675.
16. Eastmond P J: Monodehydroascorbate reductase4 is required for seed storage oil hydrolysis and postgerminative growth in *Arabidopsis*. *Plant Cell* 2007, 19:1376-1387.
17. Puttick D, Dauk M, Lozinsky S, Smith M A: Overexpression of a FAD3 desaturase increases synthesis of a polymethylene-interrupted dienoic fatty acid in seeds of *Arabidopsis thaliana* L. *Lipids* 2009, 44:753-757.
18. Lemieux B, Miguel M, Somerville C, Browse J: Mutants of *Arabidopsis* with alterations in seed lipid fatty acid composition. *Threoretical and Applied Genetics* 1990, 80:234-240.
19. Huang A H C: Oleosins and oil bodies in seeds and other organs. *Plant Physiol* 1996, 110:1055-1061.
20. Lu C-A, Lim E-K, Yu S-M: Sugar response sequence in the promoter of a rice alpha-amylase gene serves as a transcriptional enhancer. *J Biol Chem* 1998, 273:10120-10131.
21. Lu C-A, Ho T D, Ho S-L, Yu S-M: Three novel MYB proteins with one DNA binding repeat mediate sugar and hormone regulation of alpha-amylase gene expression. *Plant Cell* 2002, 14:1963-1980.
22. Stalberg K, Ellerstom M, Ezcurra I, Ablov S, Rask L: Disruption of an overlapping E-box/ABRE motif abolished high transcription of the napA storage-protein promoter in transgenic *Brassica napus* seeds. *Planta* 1996, 199:515-519.
23. Hartmann U, Sagasser M, Mehrtens F, Stracke R, Weisshaar B: Differential combinatorial interactions of cis-acting elements recognized by R2R3-MYB, BZIP, and BHLH factors control light-responsive and tissue-specific activation of phenylpropanoid biosynthesis genes. *Plant Mol Biol* 2005, 57:155-171.
24. Le B H, Cheng C, Bui A Q, Wagmaister J A, Henry K F, Pelletier J., Kwong L, Belmonte M, Kirkbride R, Horvath S, Drews G N, Fisher R L., Okamuro J K., Harada J J, Goldberg R B: Global analysis of gene activity during *Arabidopsis* seed development and identification of seed-specific transcription factors. *Proc Natl Acad Sci USA* 2010, 107:8063-8070.
25. Kurat C F, Natter K, Petschnigg J, Wolinski H, Scheuringer K, Scholz H, Zimmermann R, Leber R, Zechner R, Kohlwein S D: Obese yeast: triglyceride lipolysis is functionally conserved from mammals to yeast. *J Biol Chem* 2006, 281:491-500.
26. Eastmond P J: Cloning and characterization of the acid lipase from castor beans. *J Biol Chem* 2004, 279:45540-45545.
27. van der Schoot C, Paul L K, Paul S B, Rinne P L H: Plant lipid bodies and cell-cell signaling: A new role for an old organelle? *Plant signaling and Behavior* 2011, 6:1732-1738.
28. Kelly A L, Quettier A-L, Shaw E, Eastmond P J: Seed storage oil mobilization is important but not essential for germination or seedling establishment in *Arabidopsis*. *Plant Physiol* 2011, 157:866-875.
29. Baud S, Boutin J-P, Miguel M, Lepiniec L, Rochat C: An integrated overview of seed development in *Arabidopsis thaliana* ecotype WS. *Plant Physiol and Biochem* 2002, 40:151-160.
30. Baud S, Dubreucq B, Miguel M, Rochat C, Lepiniec L: Storage reserve accumulation in *Arabidopsis*: Metabolic and developmental control of seed filling. *The Arabidopsis Book* 2008, Vol. 6
31. Eastmond P J, Germain V, Lange P R, Bryce J H, Smith S M, Graham I A: Postgerminative growth and lipid catabolism in oilseeds lacking the glyoxylate cycle. *Proc Natl Acad Sci USA* 2000, 97:5669-5674.
32. Devanesan M G, Viruthagiri T, Sugumar N: Transesterification of *Jatropha* oil using immobilized *Pseudomonas fluorescens*. *African J of Biotechnology* 2007, 6:2497-2501.

33. Thaiyasuit P, Pianthong K, Worapun I: Acid esterification-alkaline transesterification process for methyl ester production from crude rubber seed oil. *J Oleo Sci* 2012, 61:81-88.
34. Freedman B, Pryde E H, Mounts T L: Variables affecting the yields of fatty esters from transesterified vegetable oils. *J Am Oil Chem Soc* 1984, 61:1638-1643.
35. Canakci M, van Gerpen J: Biodiesel production via acid catalysis. *Trans ASAE* 1999, 42:1203-1210.
36. Lopez D E, Goodwin J G, Bruce D A, Lotero E: Transesterification of triacetin with methanol on solid acid and base catalysts. *Appl Catalysis* 2005, 295:97-105.
37. Lopez D E, Goodwin J G, Bruce D A, Furuta S: Esterification and transesterification using modified zirconia catalysts. *Appl Catalysis* 2008, 339:76-83.
38. Clough S J, Bent A F: Floral dip: a simplified method for *Agrobacterium*-mediated transformation of *Arabidopsis thaliana*. *Plant J* 1995, 16:735-743.
39. Murashige T, Skoog F: A revised medium for rapid growth and bioassays with tobacco culture. *Physiol Plant* 1962, 15:473-497.
40. Jefferson R A, Kavanagh T A, Bevan M W: GUS fusion: β-glucuronidase as a sensitive and versatile gene fusion marker in higher plants. *EMBO J* 1987, 6:3901-3907.
41. Qiu C, Sangha J S, Song F, Zhou Z, Yin A, Gu K, Tian D, Yang J, Yin Z: Production of marker-free transgenic rice expressing tissue-specific Bt gene. *Plant Cell Reports* 2010, 29:1097-1107.
42. Guo H S, Fei J F, Xie Q, Chua N H: A chemical-regulated inducible RNAi system in plants. *Plant J* 2003, 34:383-392.
43. Mao H Z, Ye J, Chua N H: Genetic transformation of *Jatropha curcas*. 2009, International Application No.: PCT/SG2009/000479 (WO 2010/071608).
44. Li Y, Beisson F, Pollard M, Ohlrogge J: Oil content of *Arabidopsis* seeds: The influence of seed anatomy, light and plant-to-plant variation. *Pytochemistry* 2006, 67:904-915.
45. Focks N, Benning C: wrinkled1: A novel, low-seed-oil mutant of *Arabidopsis* with a deficiency in the seed-specific regulation of carbohydrate metabolism. *Plant Physiol* 1988, 118:91-101.
46. Allen G C, Flores-Vergara M A, Krasynanski S, Kumar S, Thompson W F: A modified protocol for rapid DNA isolation from plant tissues using cetyltrimethylammonium bromide. *Nat Protoc* 2006, 1:2320-2325.
47. Sambrook J, Russell D W: *Molecular cloning: a laboratory manual*. 3rd edition. Cold Spring Harbor Laboratory Press, Cold Spring Harbor, N.Y.; 2001.
Abdullah, R. et al. (2005). Immature embryo: A useful tool for oil palm (*Elaeis guineensis* Jacq.) genetic transformation studies. *Electronic Journal of Biotechnology* [online] vol. 8, no. 1 [Apr. 15, 2005). Available from: http colon // www dot ejbiotechnology dot info/content/vol8/issue1/full/1/index.html.
Chiu, W. et al. (1996). Engineered GFP as a vital reporter in plants. *Current Biology* 6:325-330.
Chowdhury, M. K. U. et al. (1997). Evaluation of five promoters for use in transformation of oil palm (*Elaeis guineensis* Jacq.) *Plant Cell Reports* 16:277-281.
Christensen, A. H. and Quail, P. H. (1989). Sequence analysis and transcriptional regulation by heat shock of polyubiquitin transcripts from maize. *Plant Mol Biol* 12:619-632.
Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.
De Wet, J. R. et al. (1987). Firefly luciferase gene: structure and expression in mammalian cells. *Mol Cell Biol* 7:725-737.
Goff, S. A. et al. (1990). Transactivation of anthocyanin biosynthetic genes following transfer of B regulatory genes into maize tissues. *EMBO J* 9:2517-2522.
Jefferson, R. A. et al. (1991). *Plant Molecular Biology Manual*, ed. Gelvin et al., Kluwer Academic Publishers, pp. 1-33.
Kain, S. R. et al. (1995). Green fluorescent protein as a reporter of gene expression and protein localization. *Biotechniques* 19:650-655.
Last, D. I. et al. (1991). pEmu: an improved promoter for gene expression in cereal cells. *Theor Appl Genet* 81:581-588.
Mash, D. I. A. et al. (2009). Transformation of oil palm using *Agrobacterium tumefaciens*. *J Oil Palm Res* 21:643-652.
McElroy, D. et al. (1990). Isolation of an efficient actin promoter for use in rice transformation. *Plant Cell* 2:163-171.
Odell, J. T. et al. (1985). Identification of DNA sequences required for activity of the cauliflower mosaic virus 35S promoter. *Nature* 313:810-812.
Omidvar, V. et al. (2008). A transient assay to evaluate the expression of polyhydroxybutyrate genes regulated by oil palm mesocarp-specific promoter. *Plant Cell Rep* 27:1451-1459.
Parveez, G. K. A. et al. (2000). Transgenic oil palm: production and projection. *Biochemical Society Transactions* 28:969-972.
Parveez, G. K. A. (2008). Biolistic mediated production of transgenic oil palm. *Methods Mol Biol* 477:301-320.
Popluechai, S., et al. (2011). *Jatropha curcas* oil body proteasome and oleosins: L-form JcOle3 as a potential phylogenetic marker. *Plant Physiol Biochem* 49: 352-356.
Velten, J. et al. (1984). Isolation of a dual plant promoter fragment from the Ti plasmid of *Agrobacterium tumefaciens*. *EMBO J* 3:2723-2730.
Zuo, J. et al. (2001). Chemical-regulated, site-specific DNA excision in transgenic plants. *Nat Biotechnol* 19:157-161.

What is claimed is:

1. A method of increasing seed oil accumulation in *Jatropha* comprising reducing the activity of a patatin-domain triacylglycerol lipase encoded by a sugar-dependent-1 (SDP1) gene in a *Jatropha* plant to cause increased seed oil accumulation, wherein the reduction in activity is achieved by an RNAi molecule comprising the nucleotide sequence set forth in SEQ ID NO:3.

2. The method of claim 1, wherein the lipase has the amino acid sequence set forth in SEQ ID NO:2.

3. The method of claim 2, wherein the lipase is encoded by a nucleic acid having a nucleotide sequence set forth in SEQ ID NO:1, or nucleotides 874-3450 of SEQ ID NO:1, or nucleotides 874-3447 of SEQ ID NO:1.

4. The method of claim 1, wherein the activity of the lipase is reduced in seeds of the *Jatropha* plant.

5. The method of claim 4, wherein the reduction in *Jatropha* seeds is accomplished using a *Jatropha* seed specific promoter.

6. The method of claim 5, wherein the *Jatropha* seed specific promoter is a *Jatropha curcas* SDP1 promoter.

7. The method of claim 6, wherein the *Jatropha curcas* SDP1 promoter has the nucleotide sequence set forth in nucleotides 1-722 of SEQ ID NO:1 or promoter functional fragment thereof.

8. The method of claim 1, wherein the seed oil accumulation is increased by about 13% to about 30%.

9. An isolated nucleic acid hairpin construct comprising nucleotides 3161-3533 of SEQ ID NO:1, wherein the nucleic acid, when used in RNAi, reduces expression of the sugar-dependent 1 (SDP1) gene.

10. The isolated nucleic acid of claim 9, wherein the nucleic acid comprises nucleotides 3161-3528 of SEQ ID NO:1.

11. The isolated nucleic acid of claim 9 which further comprises a plant operable promoter operably linked to the nucleic acid.

12. The isolated nucleic acid of claim 11, wherein the promoter is a seed specific promoter.

13. The isolated nucleic acid of claim 12, wherein the seed specific promoter is a *Jatropha curcas* SDP1 promoter.

14. The isolated nucleic acid of claim 13, wherein the *Jatropha curcas* SDP1 promoter comprises nucleotides 1-722 of SEQ ID NO:1.

15. An isolated nucleic acid comprising the nucleotide sequence set forth in SEQ ID NO:3.

16. A nucleic acid construct or a vector comprising the hairpin construct of claim 9.

17. A transgenic plant cell or transgenic plant having the hairpin construct of claim 9 stably integrated in its genome.

18. A method of making a transgenic plant cell comprising introducing the hairpin construct of claim 9 into a plant cell and selecting a transgenic plant cell in which the isolated nucleic acid is stably integrated in its genome.

19. A method of making a transgenic plant comprising introducing the hairpin construct of claim 9 into a plant cell, selecting a transgenic plant cell in which the isolated nucleic acid is stably integrated in its genome and regenerating a transgenic plant from the selected transgenic plant cell.

20. A nucleic acid molecule comprising a heterologous plant operable promoter operably linked to a nucleic acid encoding a protein comprising the amino acid sequence set forth in SEQ ID NO:2.

21. The isolated nucleic acid of claim 20 which comprises the nucleotide sequence set forth in nucleotides 874-3450 of SEQ ID NO:1 or nucleotides 874-3447 of SEQ ID NO:1.

22. The isolated nucleic acid of claim 20, wherein the promoter is a heterologous seed specific promoter.

\* \* \* \* \*